United States Patent
Hebrank et al.

(10) Patent No.: US 9,332,738 B2
(45) Date of Patent: May 10, 2016

(54) PROCESSING SYSTEM FOR TRANSFERRING EGGS, AND ASSOCIATED METHOD

(71) Applicant: Zoetis Services LLC, Florham Park, NJ (US)

(72) Inventors: John H. Hebrank, Durham, NC (US); Daniel Scott Rees, Zebulon, NC (US); Michael Glenn Schnupper, Raleigh, NC (US); Paul Archie Steen, Apex, NC (US)

(73) Assignee: Zoetis Services LLC, Florham Park, NJ (US)

( * ) Notice: Subject to any disclaimer, the term of this patent is extended or adjusted under 35 U.S.C. 154(b) by 427 days.

(21) Appl. No.: 13/901,669

(22) Filed: May 24, 2013

(65) Prior Publication Data

US 2013/0319335 A1      Dec. 5, 2013

Related U.S. Application Data

(60) Provisional application No. 61/655,561, filed on Jun. 5, 2012, provisional application No. 61/822,652, filed on May 13, 2013.

(51) Int. Cl.
*A01K 45/00* (2006.01)
*A01K 43/00* (2006.01)
*A61D 1/02* (2006.01)

(52) U.S. Cl.
CPC ............... *A01K 43/00* (2013.01); *A01K 45/007* (2013.01); *A61D 1/025* (2013.01)

(58) Field of Classification Search
CPC ..... A01K 45/007; A01K 45/00; A01K 43/00; A01K 43/04; A01K 11/006; A01K 29/005; A01K 43/005; A61D 1/025

USPC ................... 119/6.8, 338, 348, 322
See application file for complete search history.

(56) References Cited

U.S. PATENT DOCUMENTS

| | | | | |
|---|---|---|---|---|
| 5,784,992 A * | 7/1998 | Petitte | ................ | A01K 67/0275 119/174 |
| 5,898,488 A | 4/1999 | Kuhl | | |
| 6,213,709 B1 | 4/2001 | Hebrank | | |
| 7,041,439 B2 | 5/2006 | Phelps et al. | | |
| 7,333,187 B2 * | 2/2008 | Hebrank | ................ | G01N 33/08 119/6.8 |
| 7,721,674 B2 * | 5/2010 | Smith | .................... | A61D 1/025 119/6.8 |
| 8,201,518 B2 * | 6/2012 | Smith | .................... | A61D 1/025 119/6.6 |
| 8,297,227 B2 * | 10/2012 | Breuil | .................. | A01K 45/007 119/6.6 |
| 8,479,684 B2 * | 7/2013 | Nadreau | .................. | A23B 5/20 119/6.8 |
| 2014/0014040 A1 * | 1/2014 | Mukaddam | .......... | A01K 45/007 119/6.8 |

OTHER PUBLICATIONS

International Search Report and Written Opinion, International Application PCT/US2013/042809, Date of Mailing Jul. 31, 2013.

\* cited by examiner

*Primary Examiner* — Yvonne Abbott-Lewis
(74) *Attorney, Agent, or Firm* — Scott C. Mayhew

(57) ABSTRACT

An egg transfer system is provided. Such an egg transfer system includes a controller configured to receive a classification signal indicative of an egg classification status for each of a plurality of eggs carried by a flat. A transfer head assembly is in communication with the controller and is configured to remove a plurality of eggs from the flat. The eggs are grouped into at least a first and second subset based on the egg classification status. The controller is configured to direct the transfer head assembly to selectively release the first and second subsets separately based on the respective egg classification status of the eggs. An associated method is also provided.

18 Claims, 22 Drawing Sheets

PROCESSING SYSTEM FOR TRANSFERRING EGGS, AND ASSOCIATED METHOD

CROSS REFERENCE TO RELATED APPLICATIONS

This application claims priority from U.S. Provisional Patent Application Nos. 61/655,561, filed Jun. 5, 2012, and 61/822,652, filed May 13, 2013, both of which are incorporated herein by reference in their entirety.

TECHNICAL FIELD

The present disclosure generally relates to egg transfer systems. More particularly, the present disclosure relates to an egg transfer system capable of selectively sorting incubated eggs according to an egg classification scheme, and an associated method.

BACKGROUND

Mechanical devices are used to transfer avian eggs within a poultry hatchery from one processing station to another processing station throughout an incubation cycle for hatching viable eggs. For example, such devices may be used to facilitate or otherwise aid transfer of the eggs from a climate controlled setter incubator to a climate controlled hatcher incubator where newborn chicks are hatched. In this regard, the eggs are typically stored in various trays or containers throughout the incubation cycle. The eggs are typically transferred from one tray associated with the setter incubator to another type of tray associated with the hatcher incubator. Typically, the setter incubator tray is configured differently than the hatcher incubator tray. For example, the setter incubator tray (commonly referred to as a "flat") may include receptacles capable of receiving the eggs individually and maintaining the eggs in an upright orientation, while the hatcher incubator tray (commonly referred to as a "hatching basket") may be an open-ended container without receptacles such that the avian eggs are not restricted and ready for hatch.

In some instances, the eggs transferred between the flats and the hatching baskets may contain various classifications of eggs. For example, the flats may contain both viable and non-viable eggs, which are then transferred to the hatching basket. Placement of the non-viable eggs into the hatching basket can have a negative impact on hatch and chick quality. Further, the non-viable eggs have value in that such non-viable eggs may be sold to other industries for use (e.g., pet food industry).

Furthermore, the flats may contain both male and female eggs, which are then transferred to the hatching basket. Separation of eggs according to gender prior to hatch is desirable for certain poultry industries, particularly the layer and breeder industries.

Accordingly, it would be desirable to provide an egg transfer system capable of selectively sorting and transferring eggs according to egg classification. Furthermore, it would be desirable to provide an associated method that would facilitate selective sorting and transfer of eggs according to egg classification.

BRIEF SUMMARY

The above and other needs are met by aspects of the present disclosure which, according to one aspect, provides an egg processing system having a controller configured to receive a classification signal indicative of an egg classification status for each of a plurality of eggs carried by an egg carrier. A transfer head assembly is in communication with the controller and is configured to remove a plurality of eggs from the egg carrier. The eggs are grouped into at least a first and second subset based on the egg classification status. The controller is configured to direct the transfer head assembly to selectively release the first and second subsets separately based on the respective egg classification status of the eggs.

Another aspect provides a method of processing eggs. The method comprises transporting a plurality of eggs in an egg carrier tray to a classification device. The method further comprises classifying the eggs using the classification device so as to assign each egg an egg classification status. The eggs are classified as being associated with one of a first subset and a second subset of the eggs according to the egg classification status. The method further comprises concurrently lifting the first and second subsets of eggs from the egg carrier tray using a transfer head assembly. The method further comprises selectively releasing one of the first and second subsets of eggs from the transfer head assembly. The method further comprises releasing the other one of the first and second subsets of eggs from the transfer head assembly.

Thus, various aspects of the present disclosure provide advantages, as otherwise detailed herein.

BRIEF DESCRIPTION OF THE DRAWINGS

Figure 1:
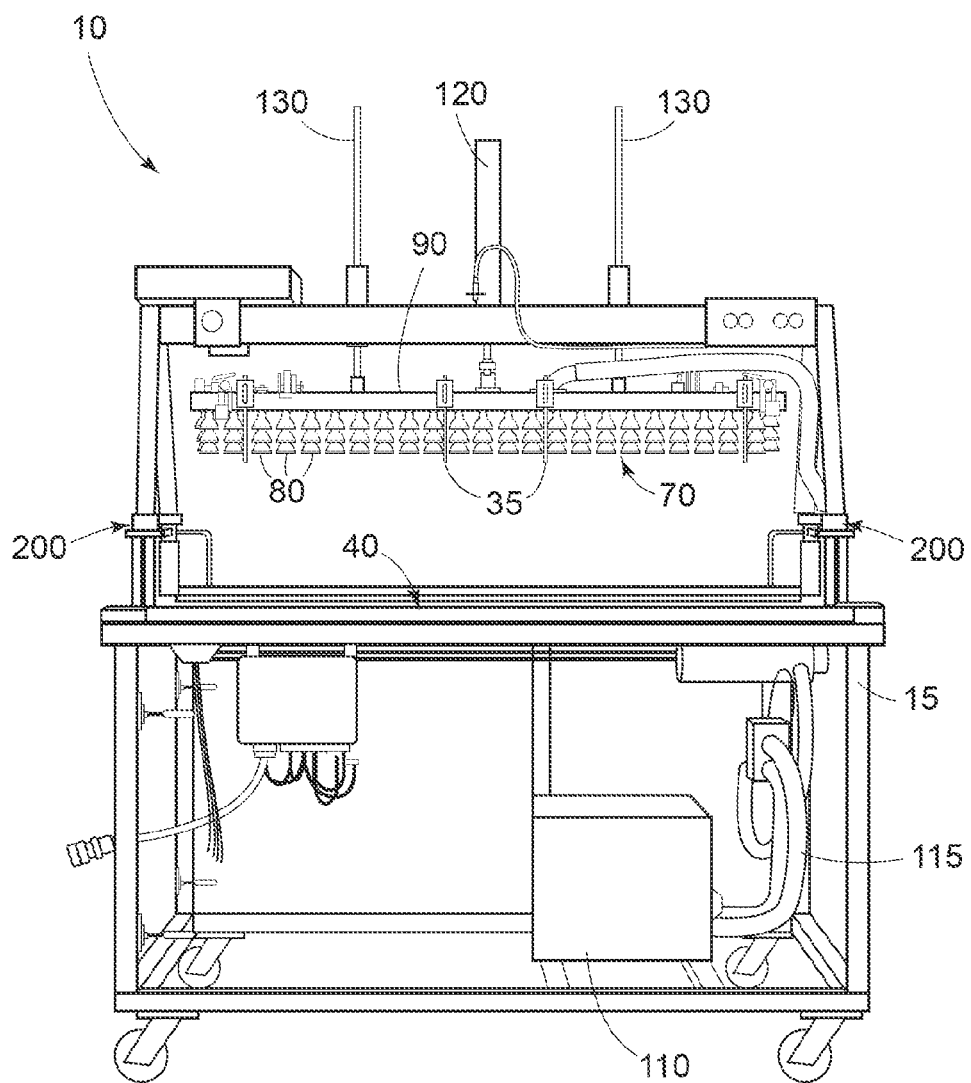
Figure 2:
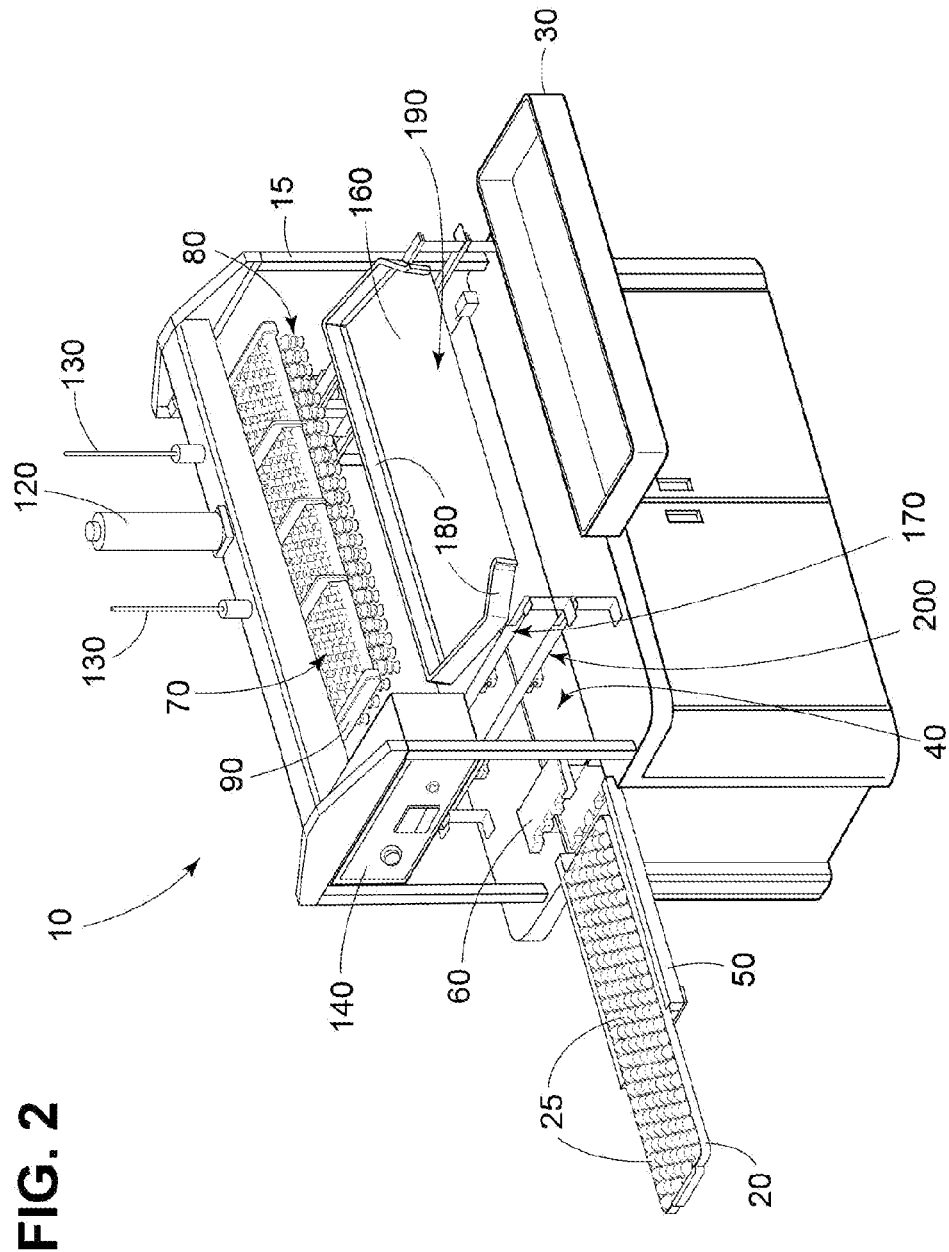
Figure 3:
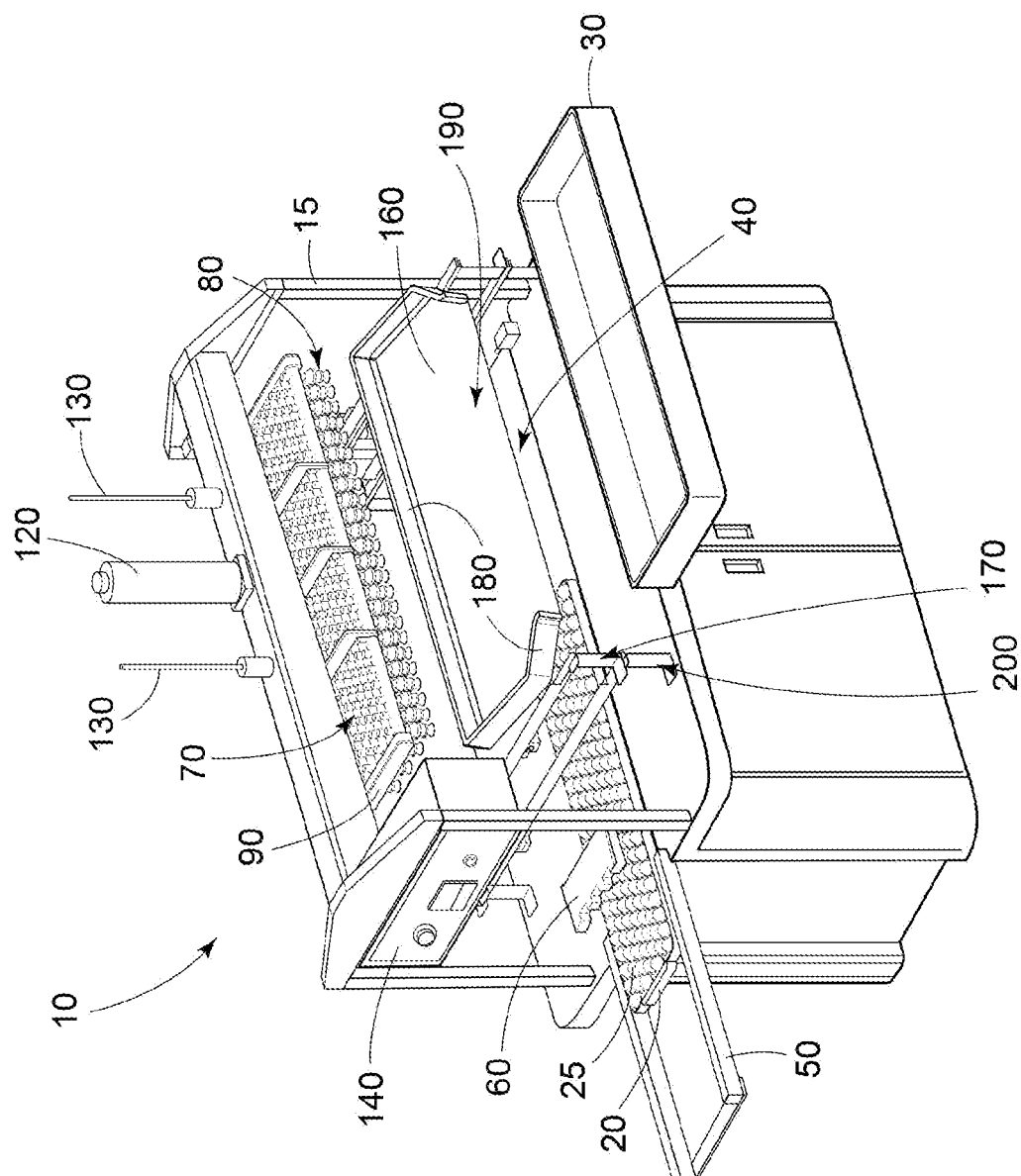
Figure 4:
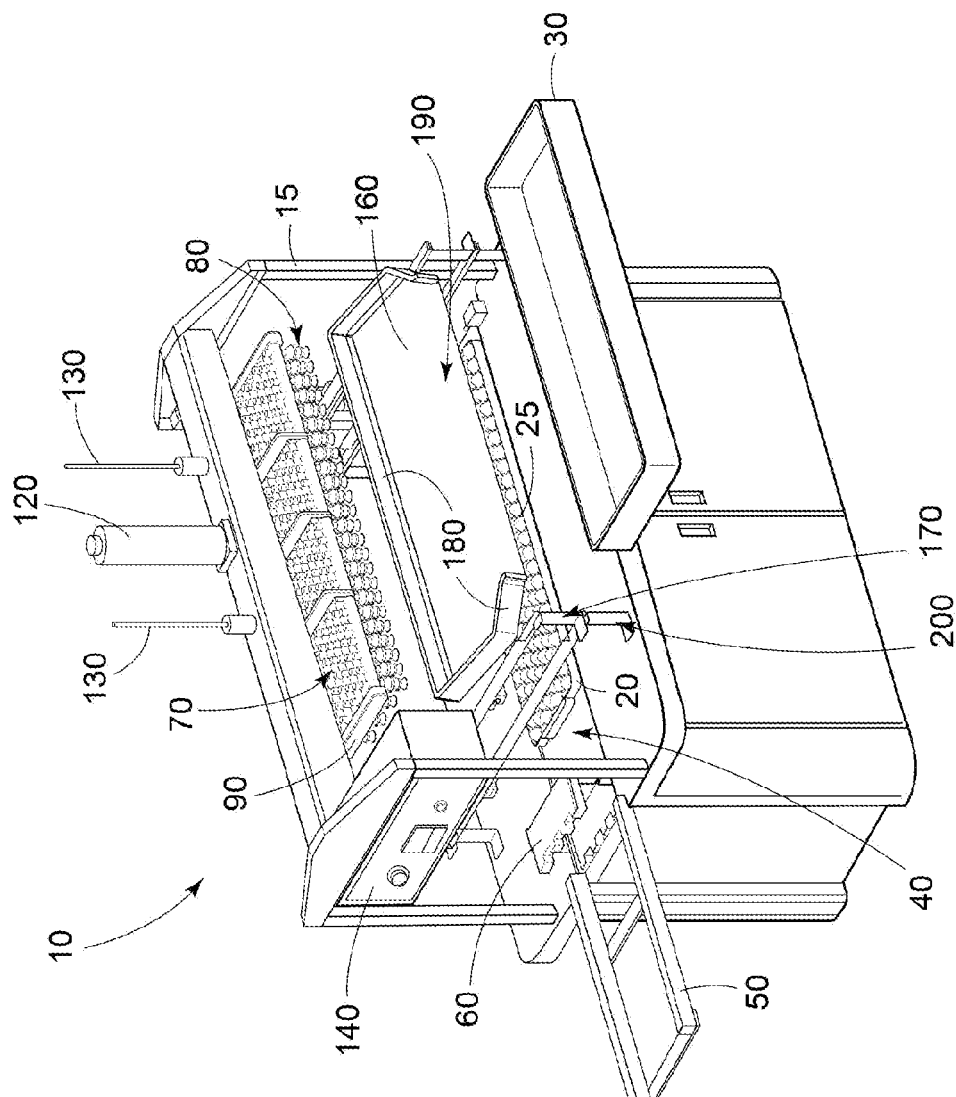
Figure 5:
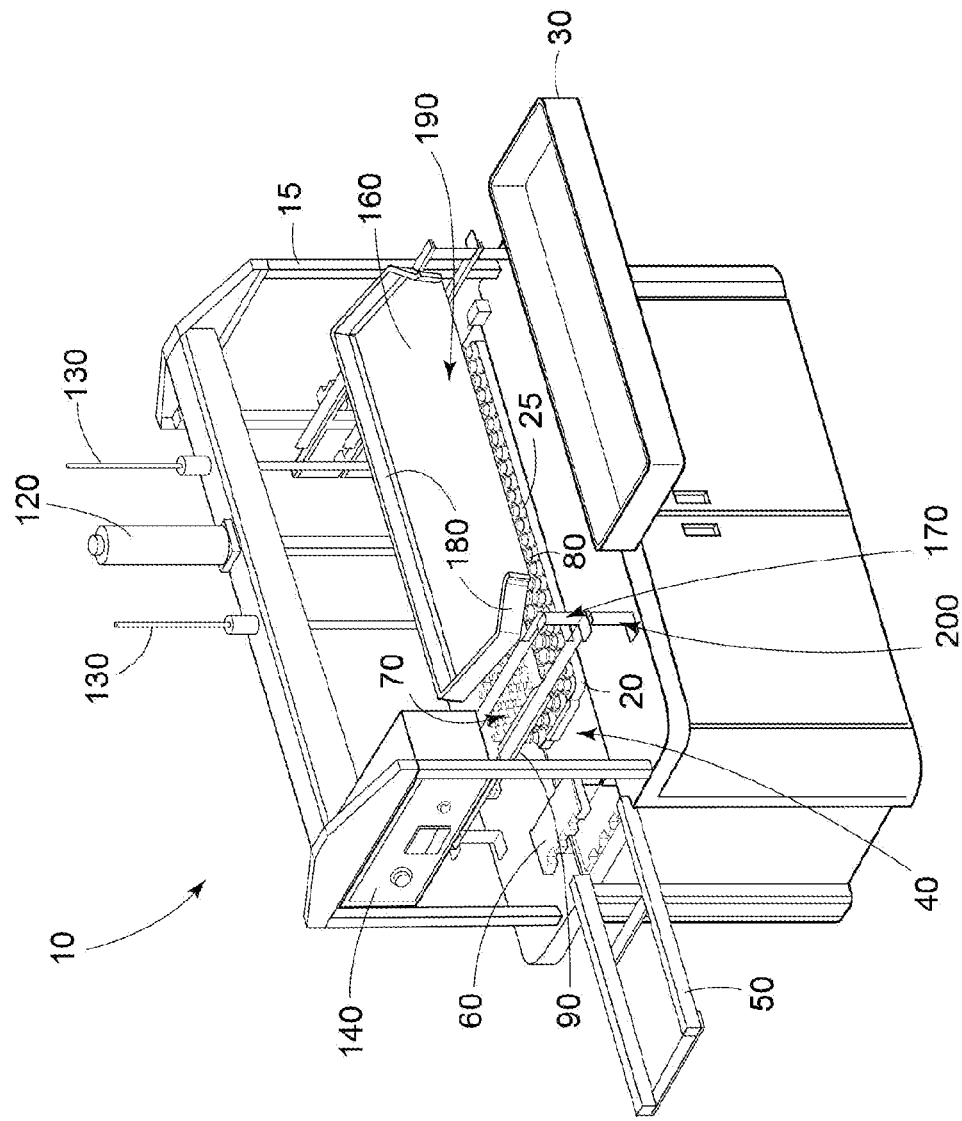
Figure 6:
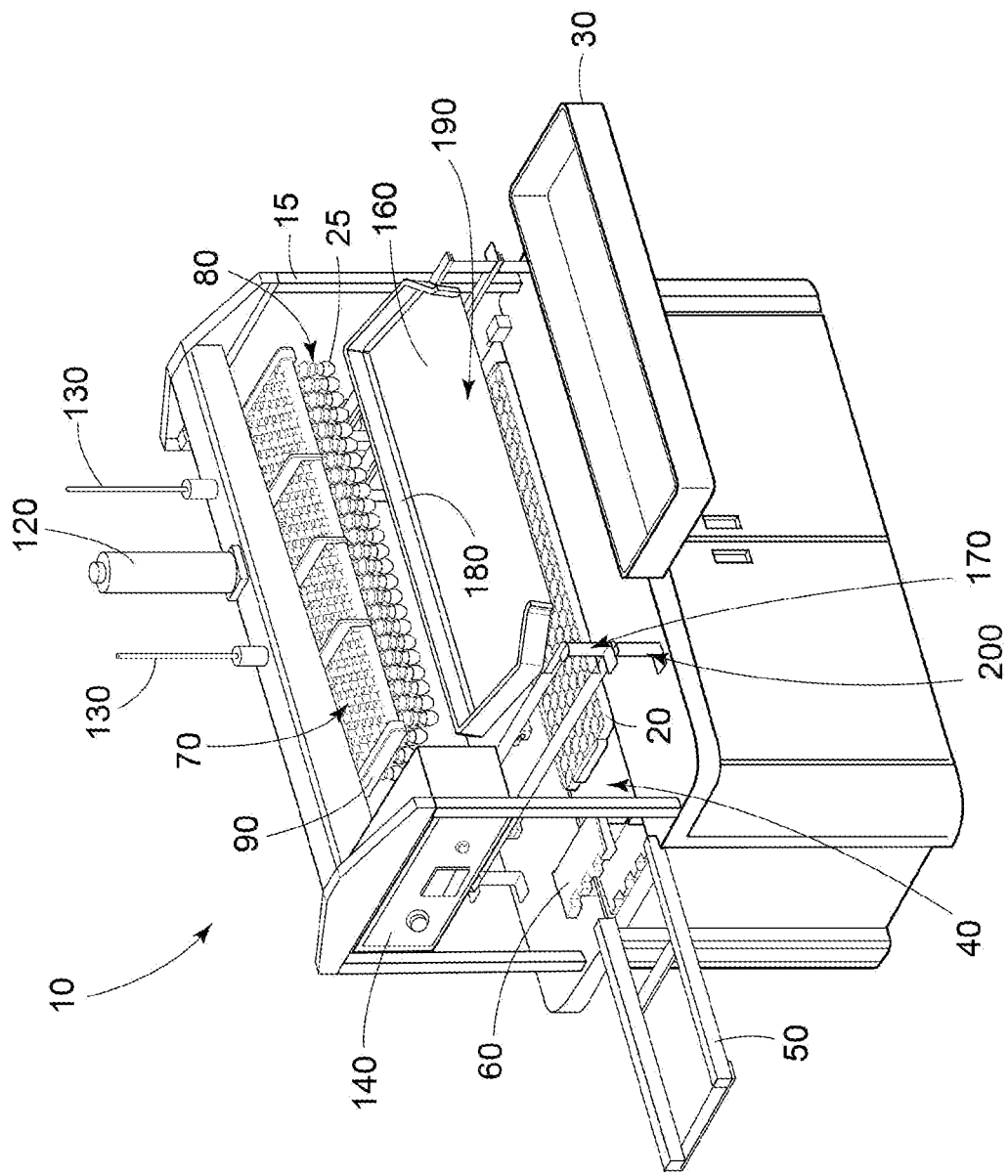
Figure 7:
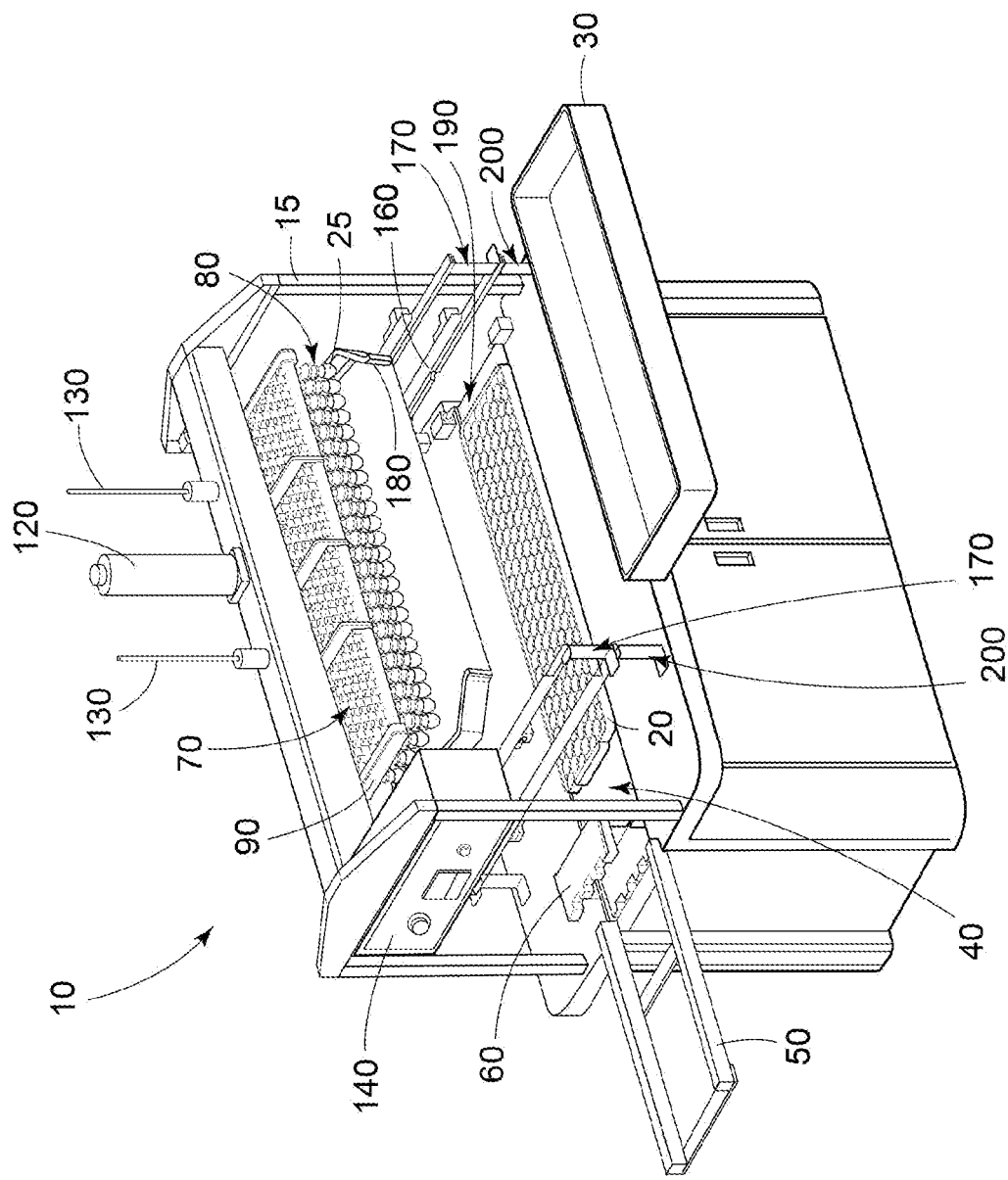
Figure 8:
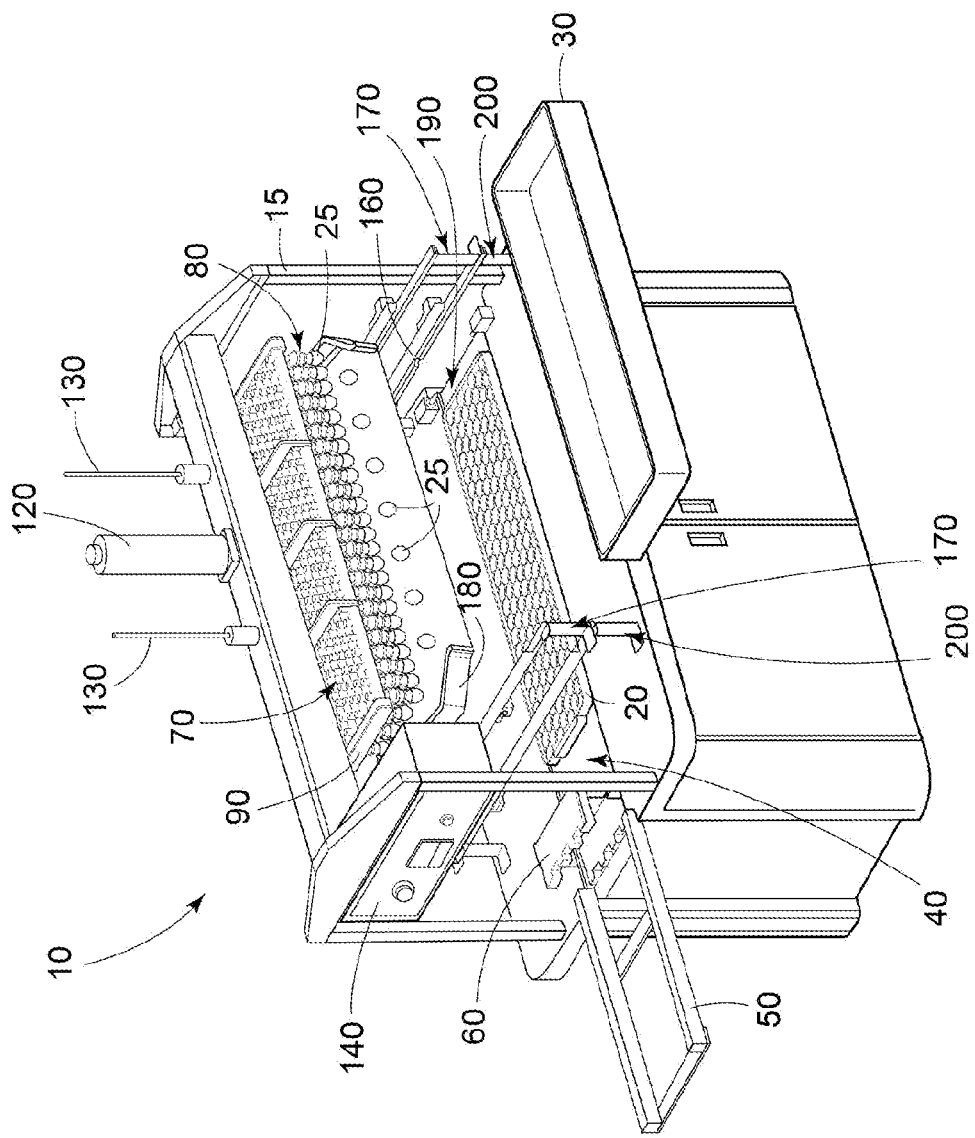
Figure 9:
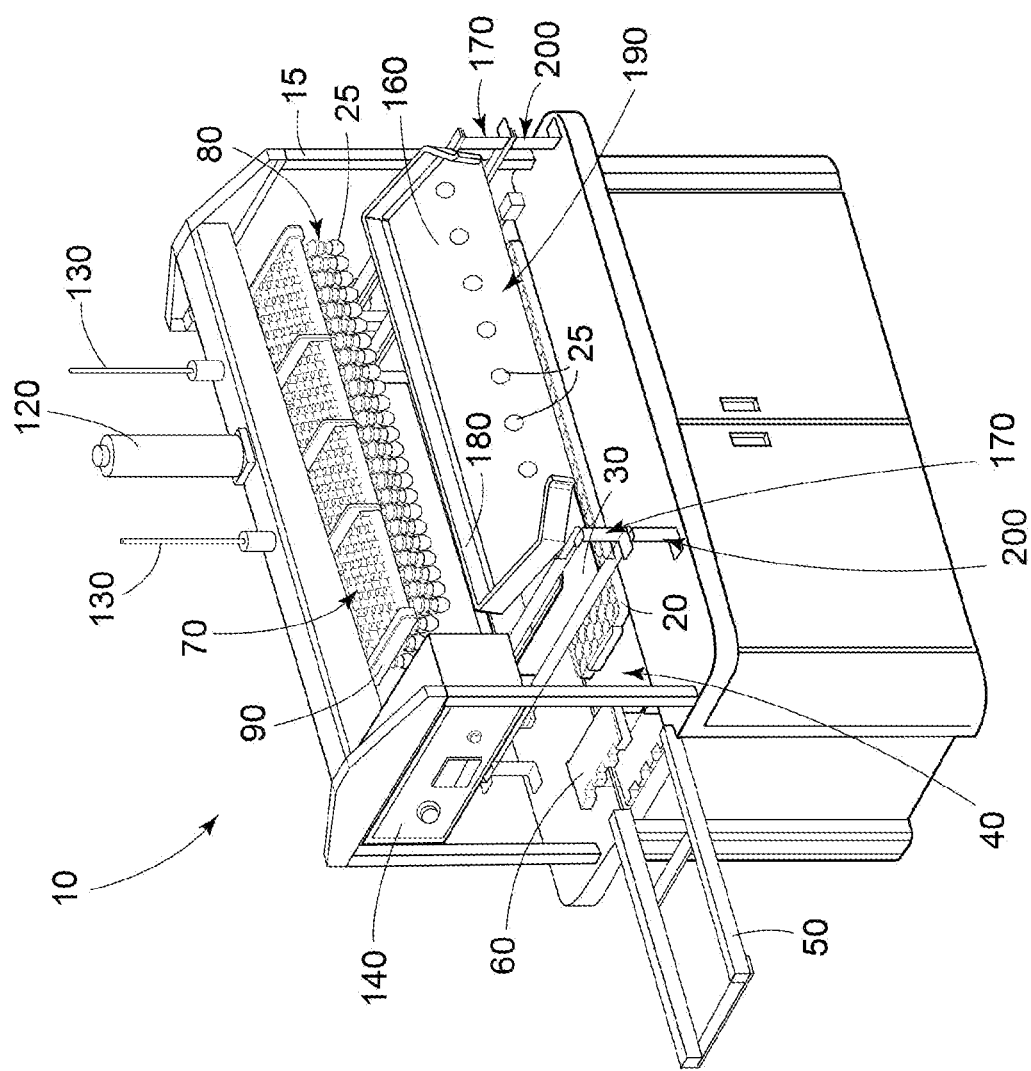
Figure 10:
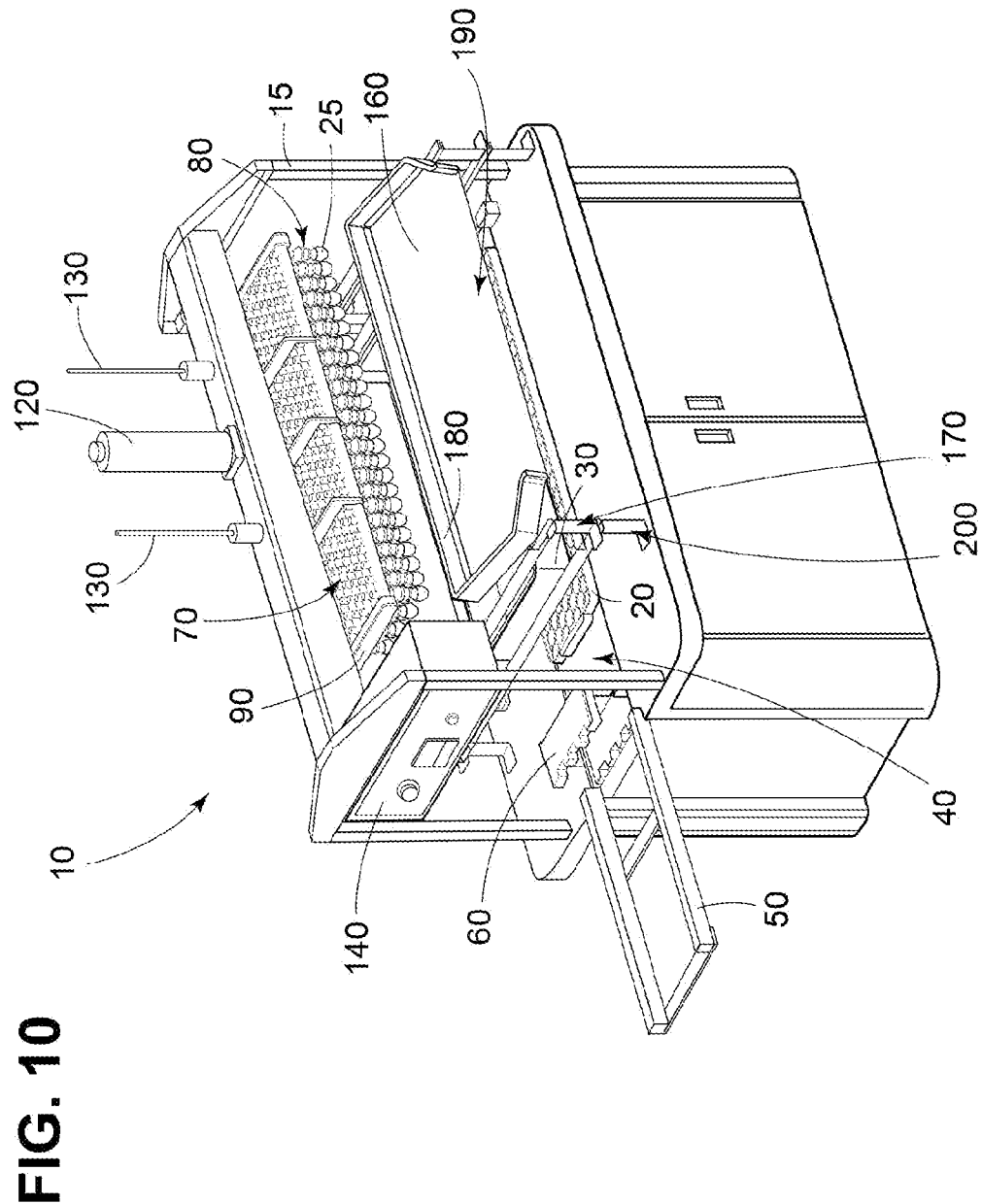
Figure 11:
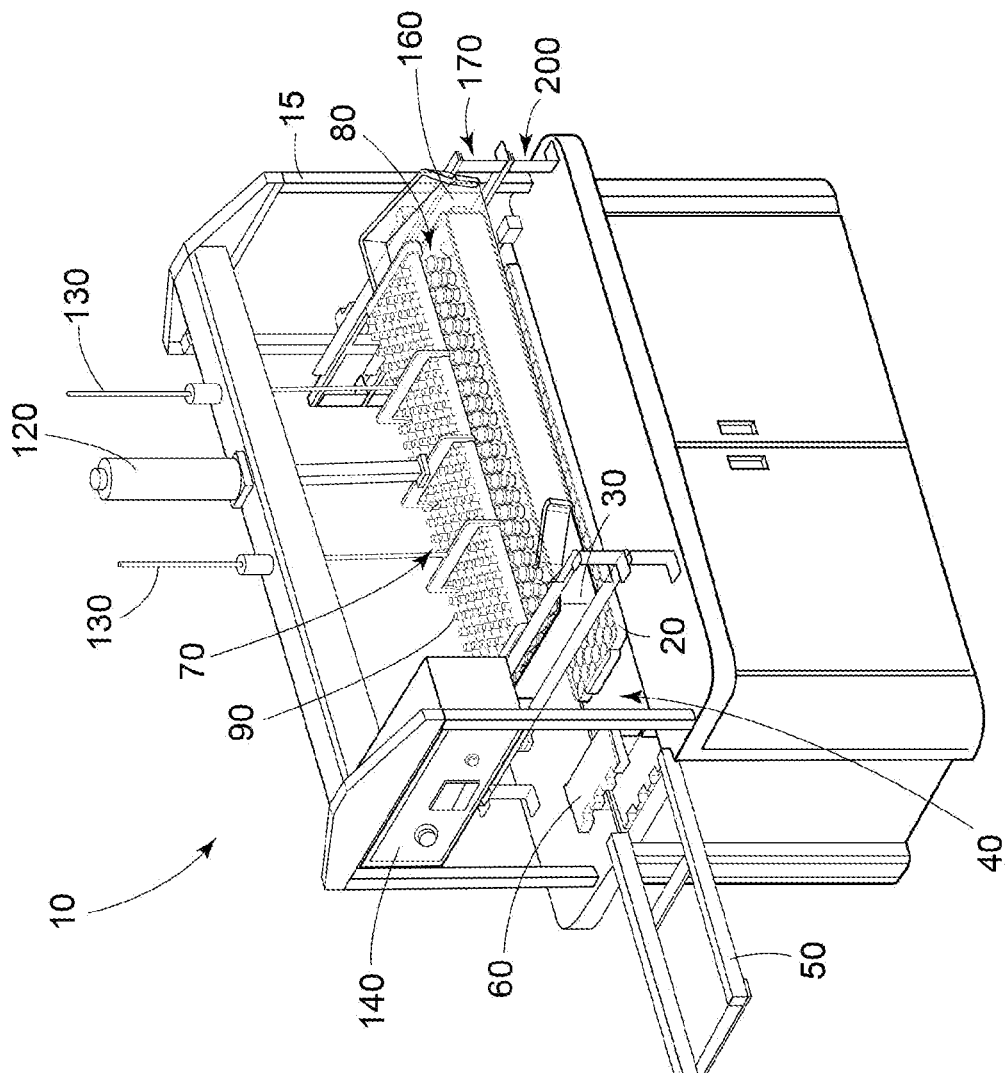
Figure 12:
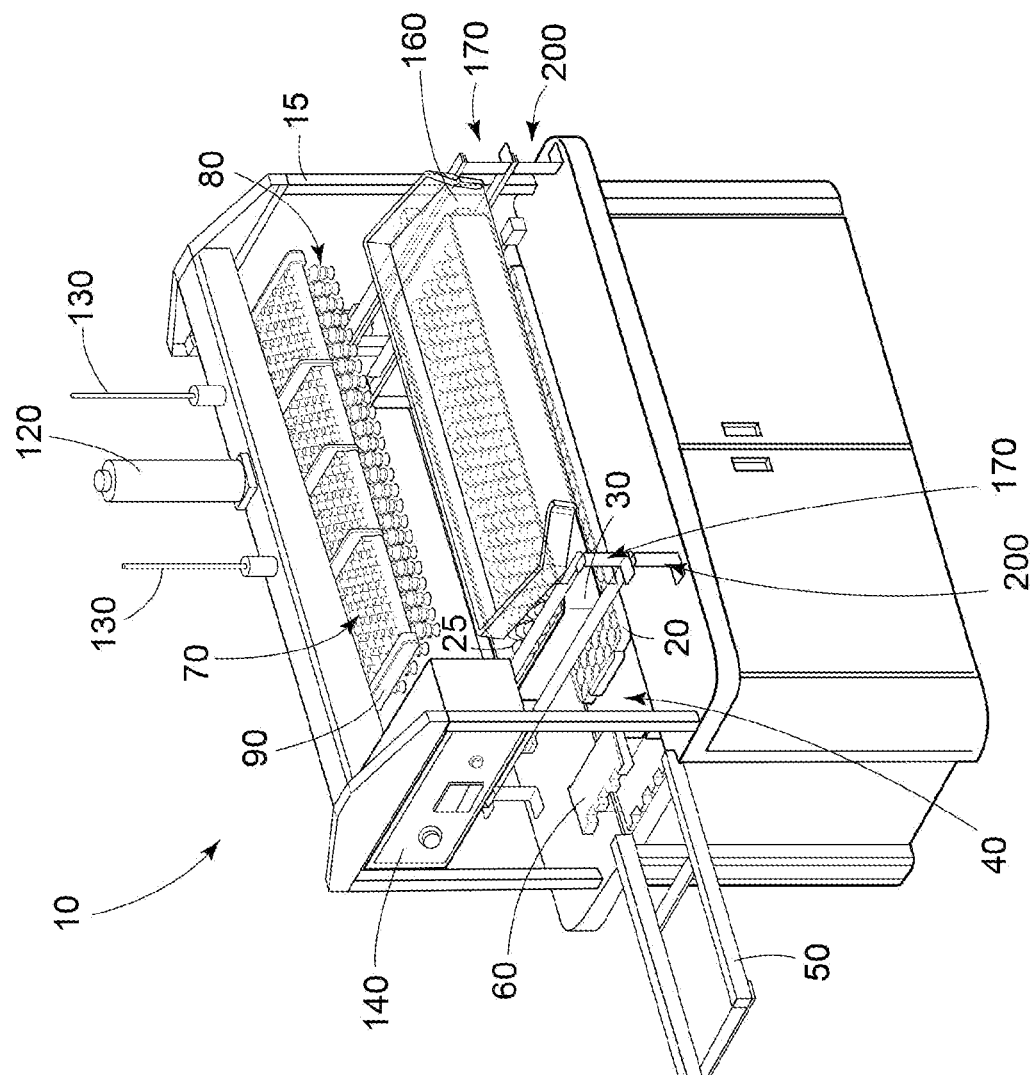
Figure 13:
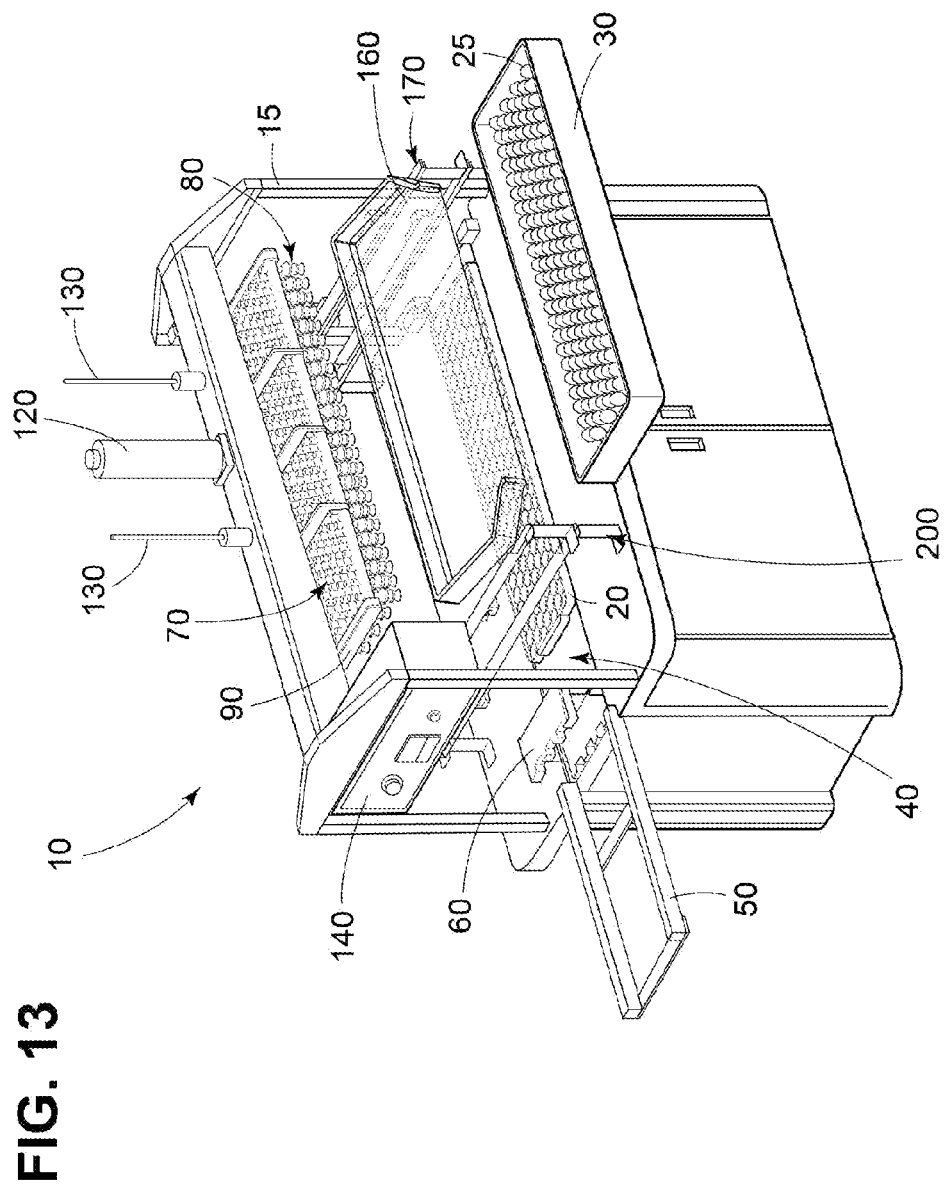
Figure 14:
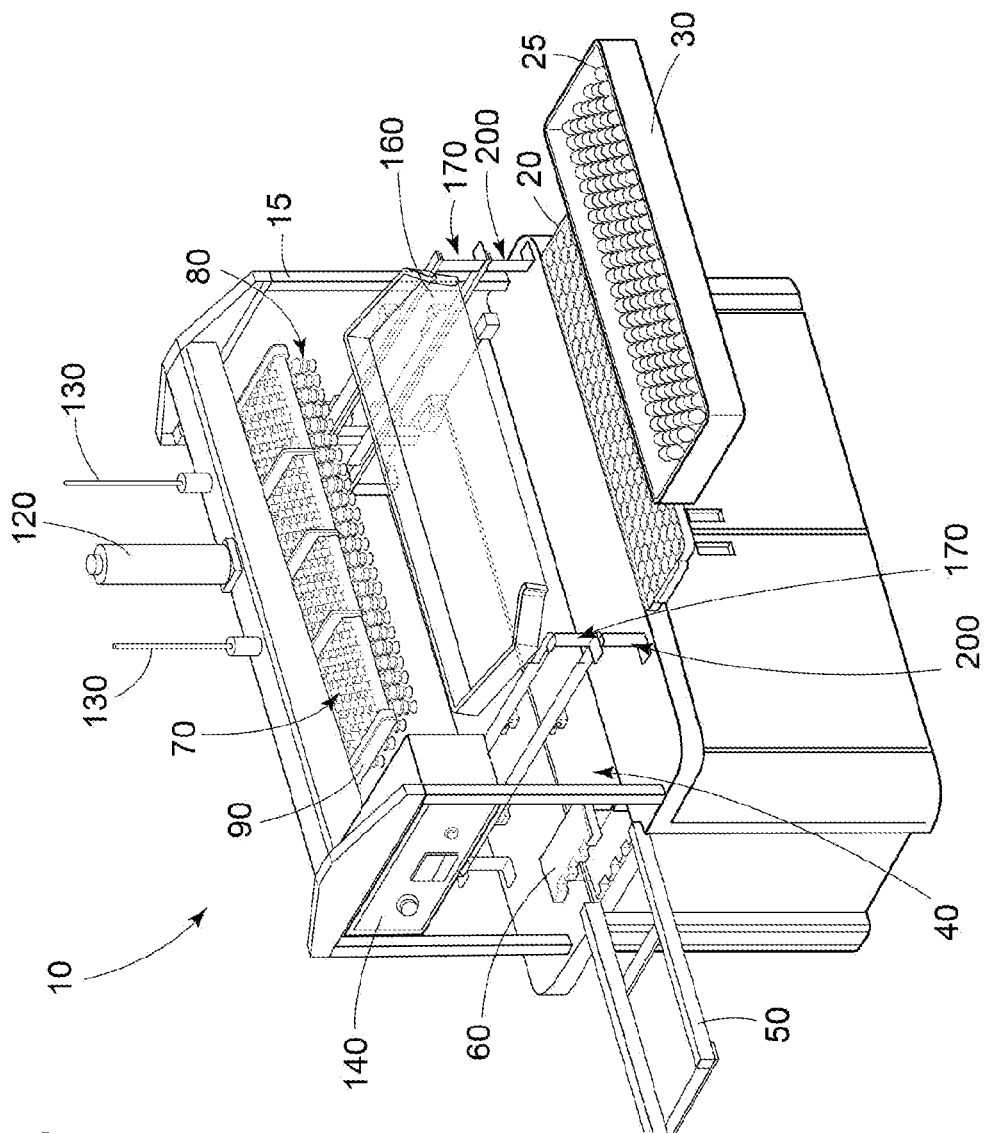
Figure 15:
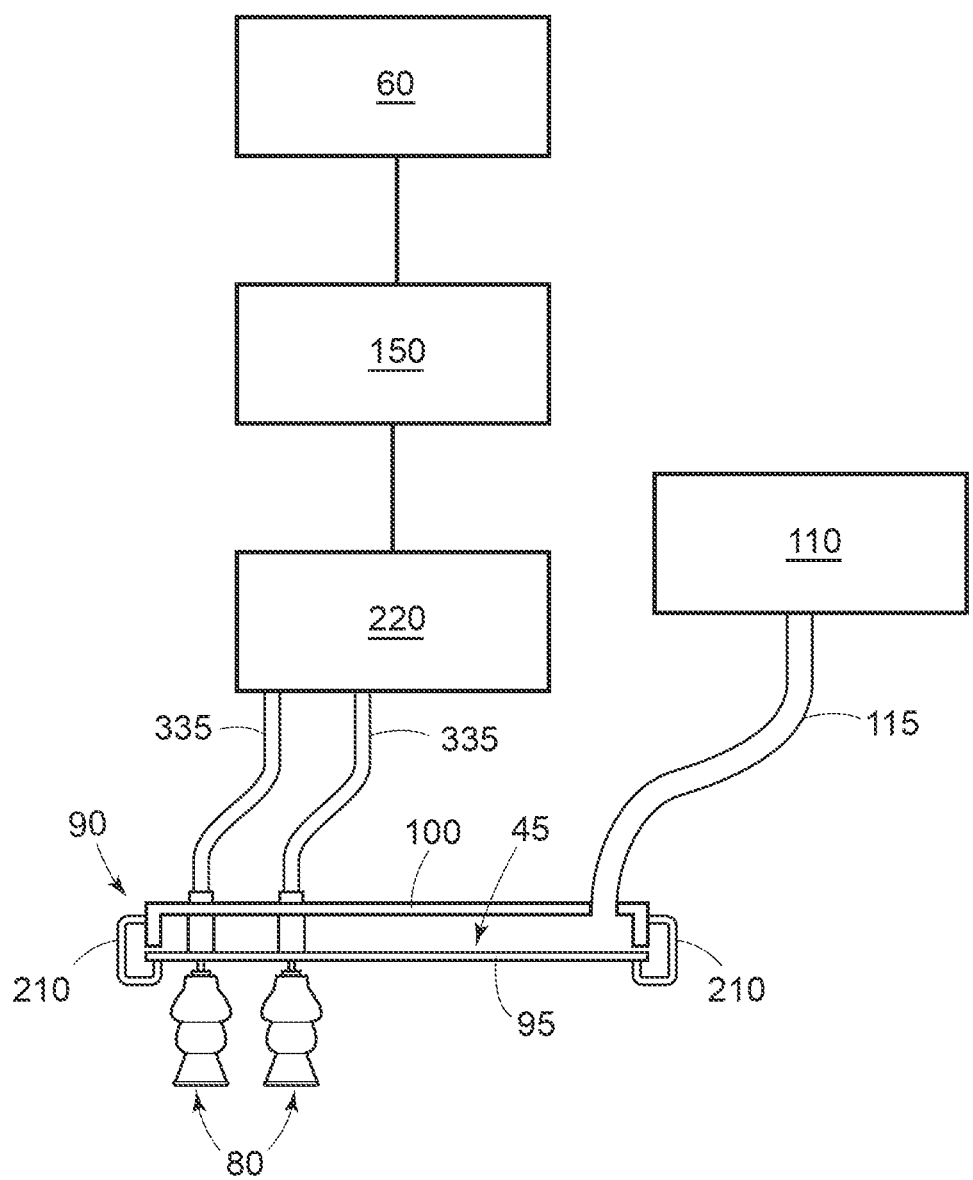
Figure 16:
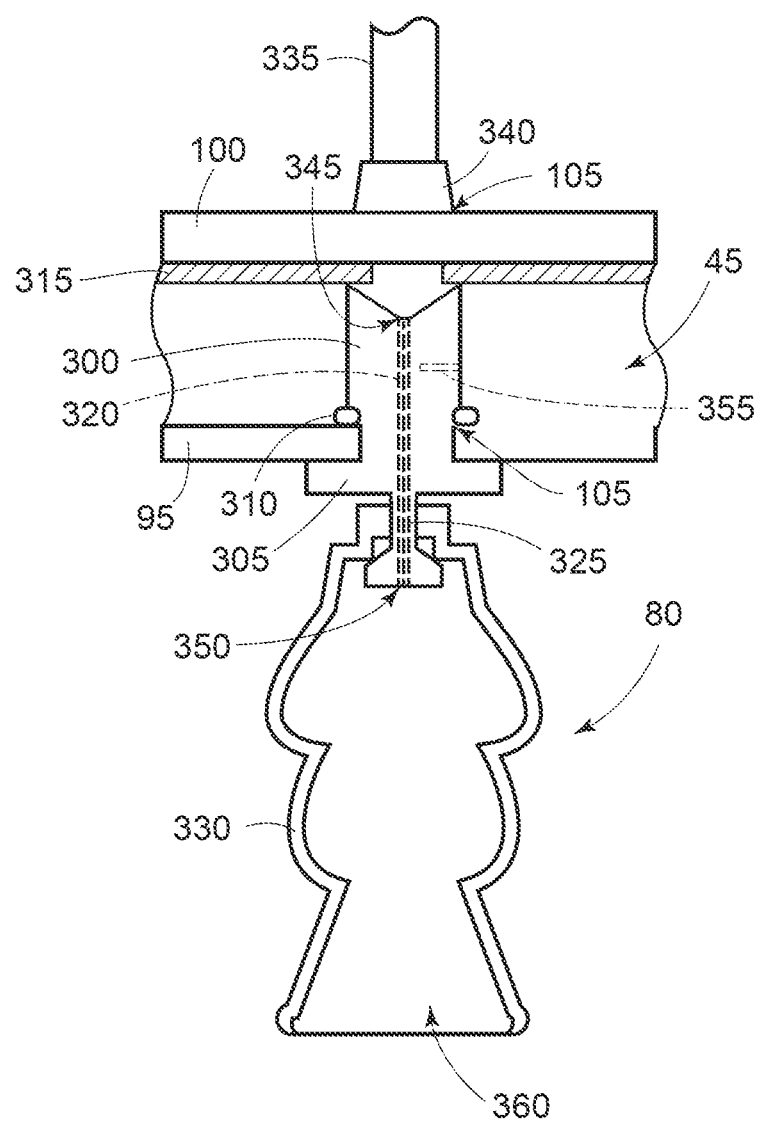
Figure 17:
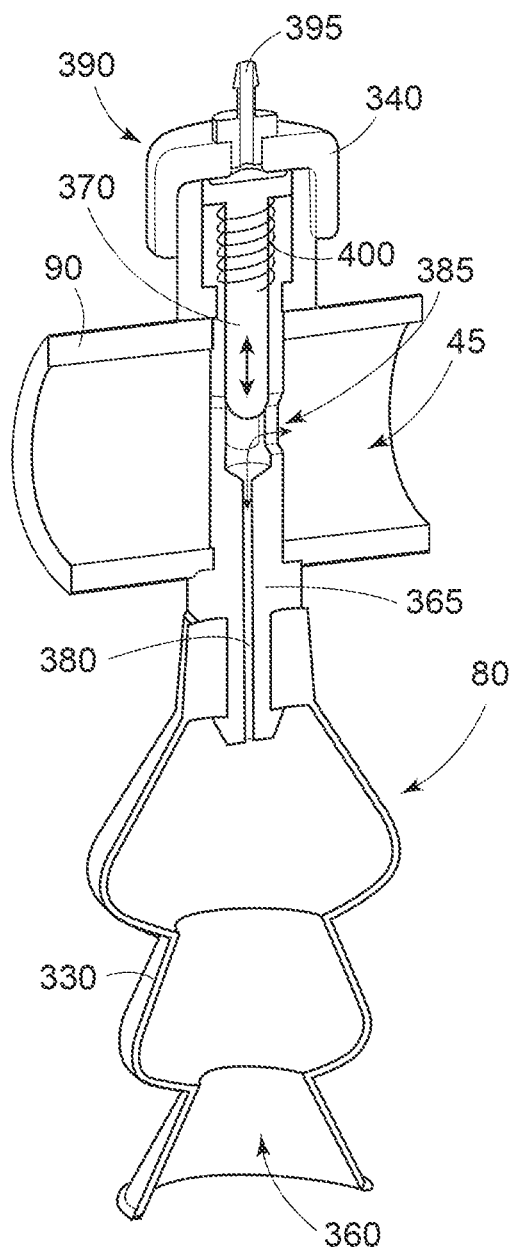
Figure 18:
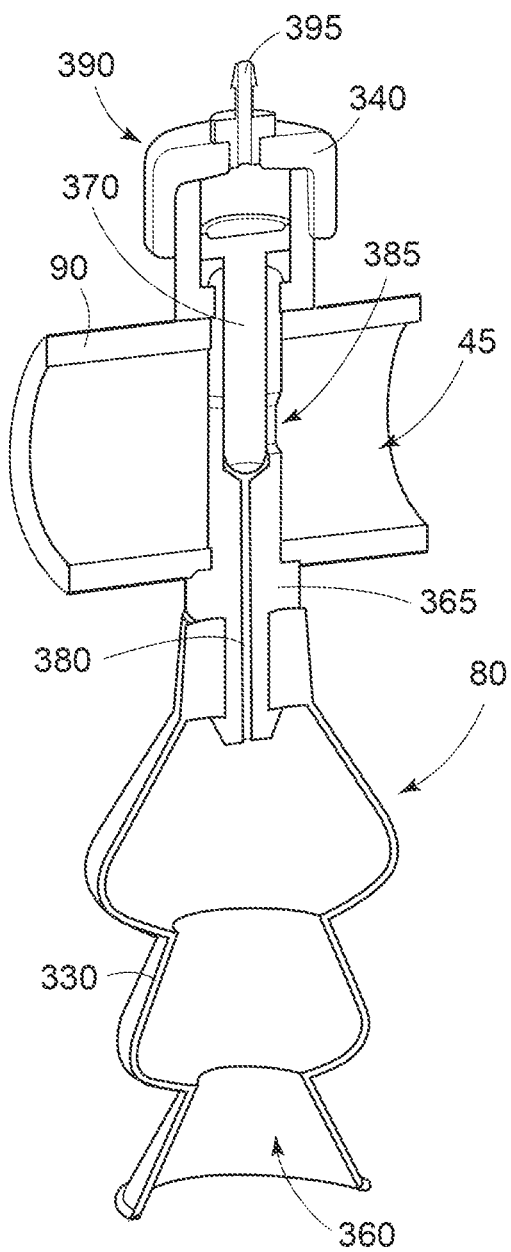
Figure 19:
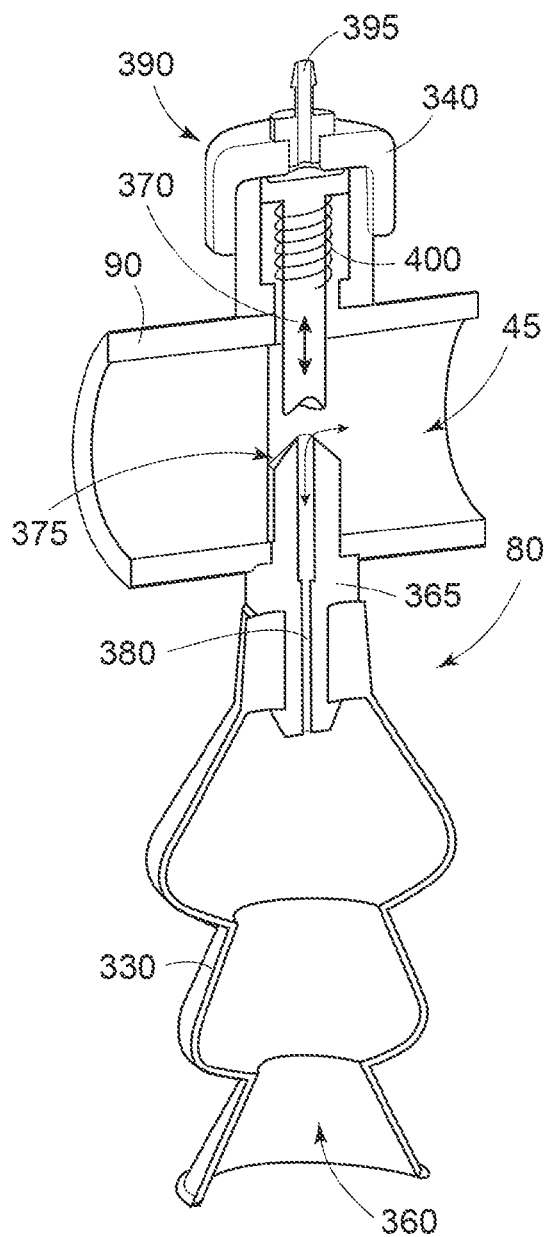
Figure 20:
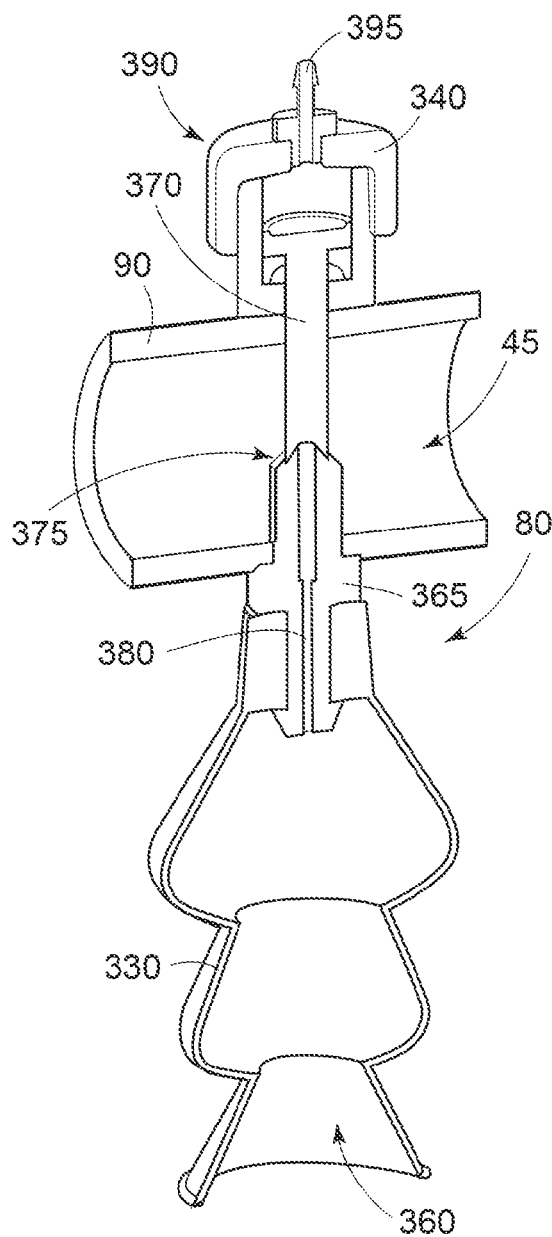
Figure 21:
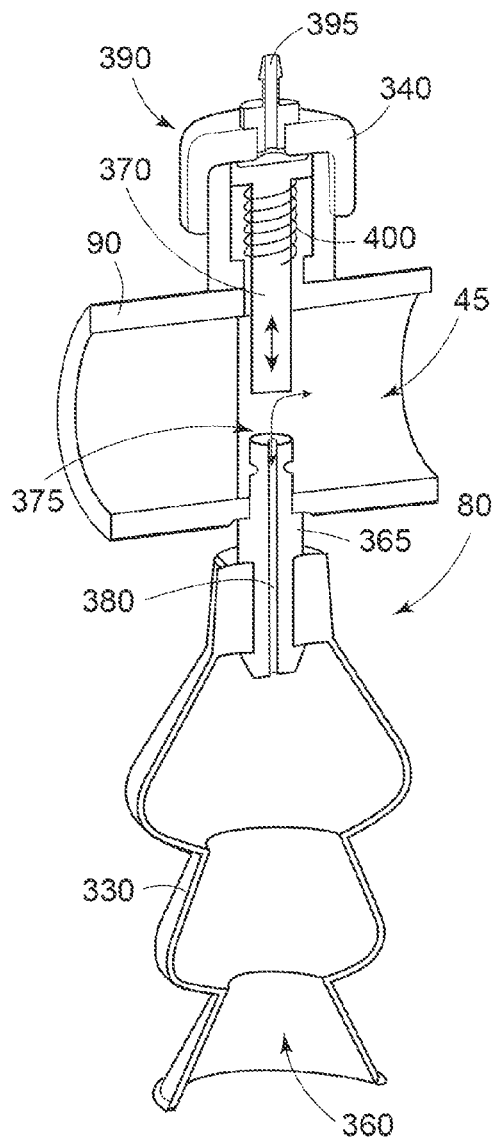
Figure 22:
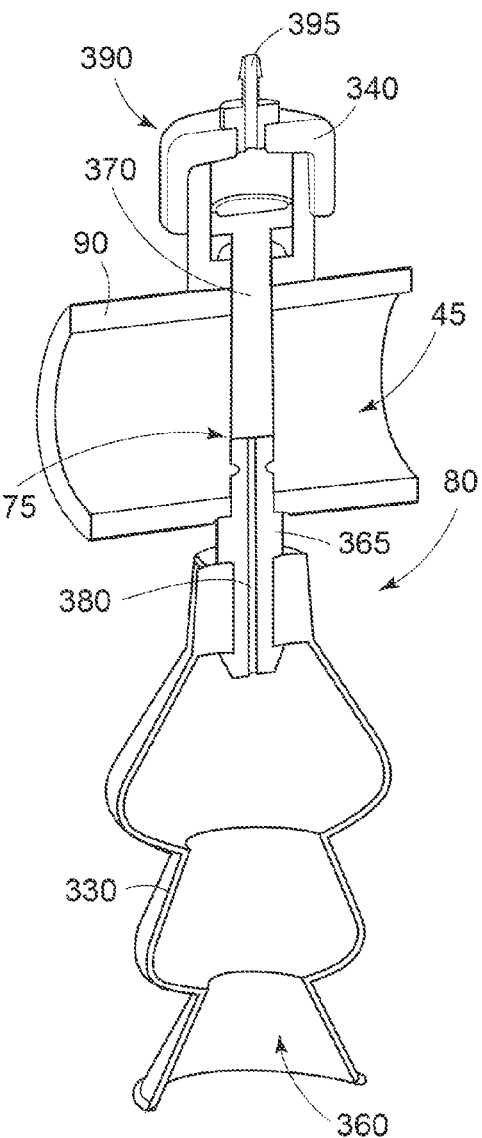
Figure 23:
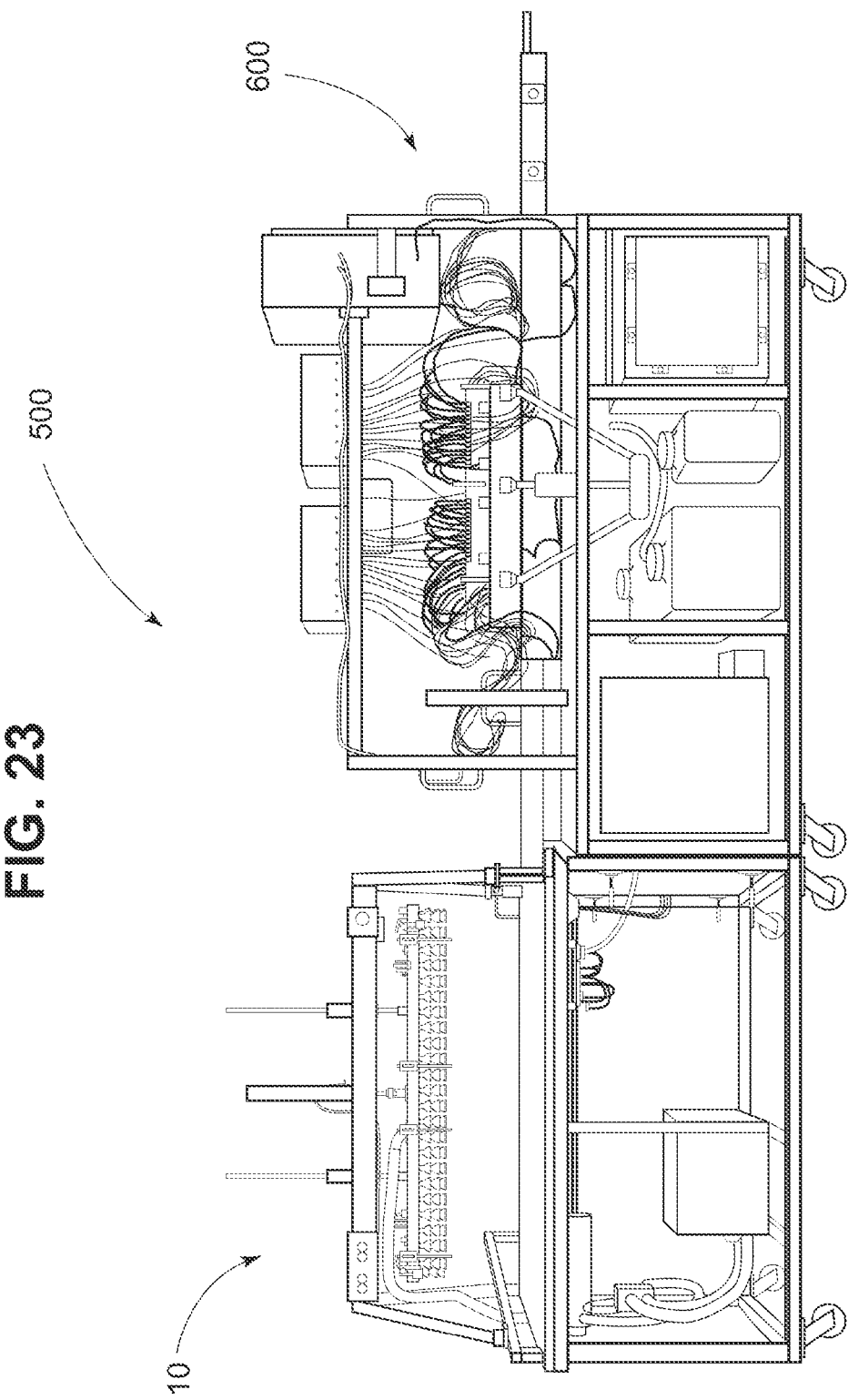
Figure 24:
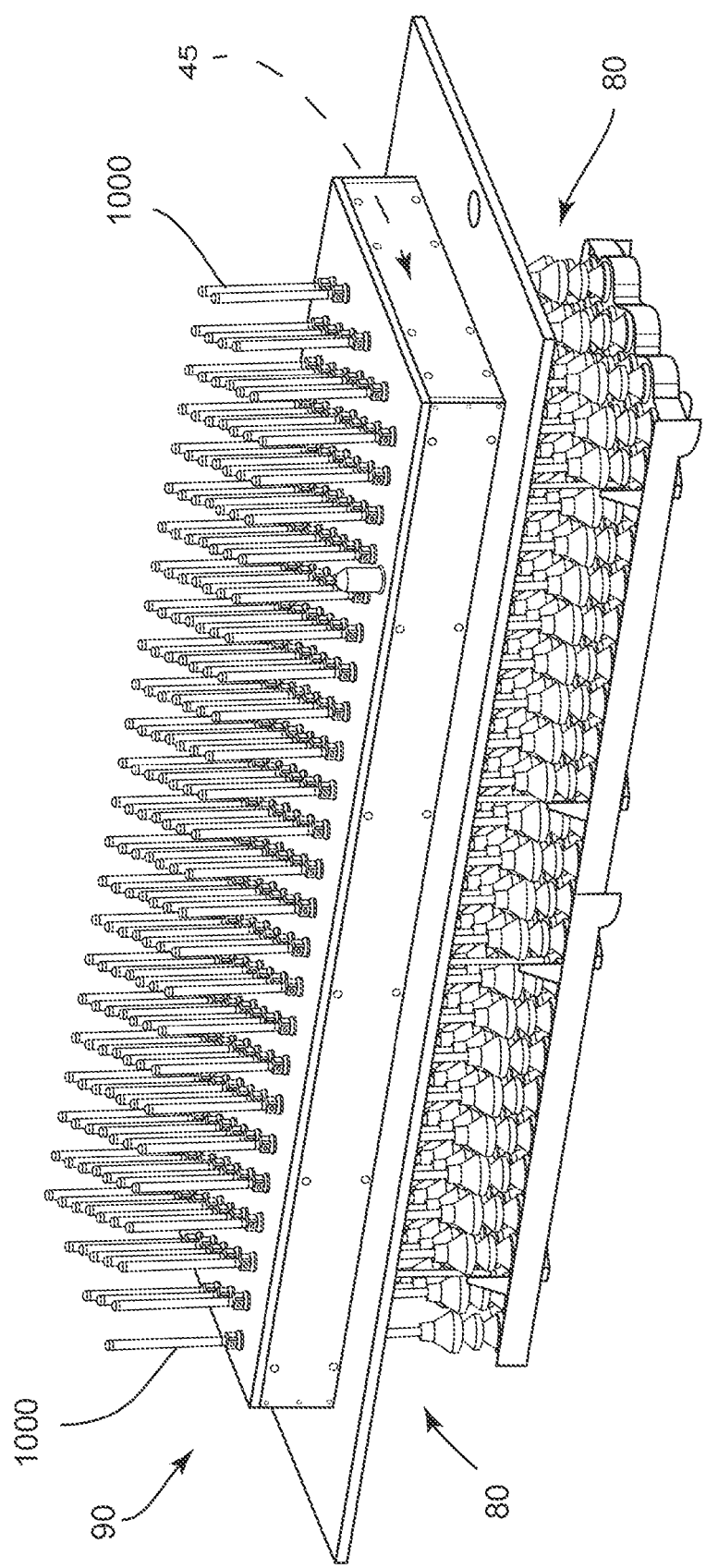
Figure 25:
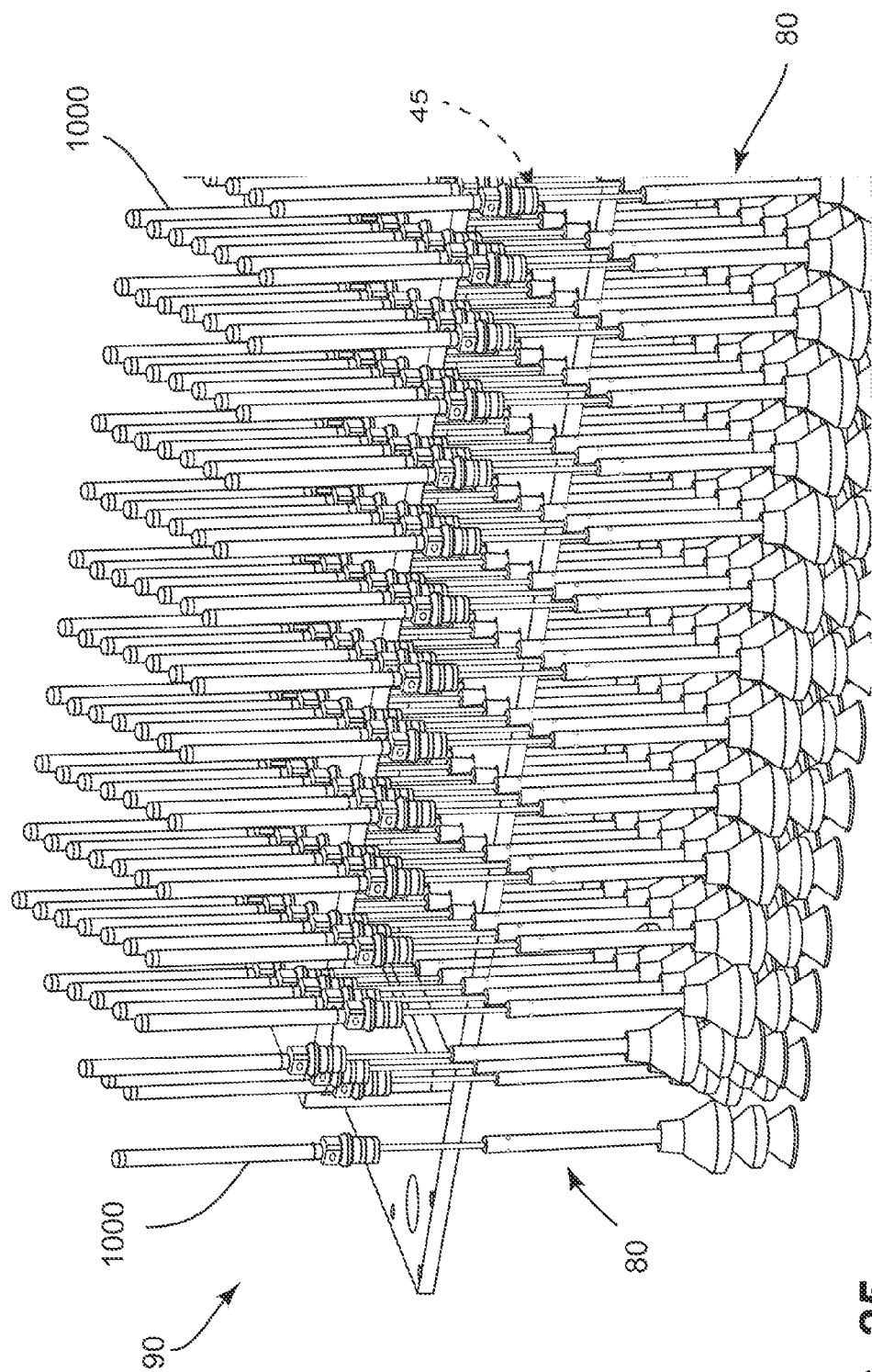

Having thus described various embodiments of the present disclosure in general terms, reference will now be made to the accompanying drawings, which are not necessarily drawn to scale, and wherein:

FIG. 1 is a side view of an egg transfer system capable of implementing selective sorting of a plurality of avian eggs, according to one aspect of the present disclosure;

FIG. 2 is a schematic perspective view of an egg transfer system, according to one aspect of the present disclosure, illustrating a plurality of eggs carried by a flat being conveyed to a transfer position;

FIG. 3 is a schematic perspective view of the egg transfer system of FIG. 2, illustrating the eggs being further conveyed to the transfer position;

FIG. 4 is a schematic perspective view of the egg transfer system of FIG. 2, illustrating the eggs in the transfer position beneath a transfer head assembly;

FIG. 5 is a schematic perspective view of the egg transfer system of FIG. 2, illustrating the transfer head assembly descending to engage the eggs;

FIG. 6 is a schematic perspective view of the egg transfer system of FIG. 2, illustrating the transfer head assembly lifting the eggs from the flat;

FIG. 7 a schematic perspective view of the egg transfer system of FIG. 2, illustrating an egg discard receptacle moving to a position beneath the transfer head assembly;

FIG. 8 is a schematic perspective view of the egg transfer system of FIG. 2, illustrating multiple eggs identified as non-viable being selectively released into the egg discard receptacle;

FIG. 9 is a schematic perspective view of the egg transfer system of FIG. 2, illustrating the egg discard receptacle moving to an egg removal position and a hatching basket moving to a loading position;

FIG. 10 is a schematic perspective view of the egg transfer system of FIG. 2, illustrating removal of the non-viable eggs from the egg discard receptacle;

FIG. 11 is a schematic perspective view of the egg transfer system of FIG. 2, illustrating the transfer head descending to the hatching basket for release of the viable eggs thereinto;

FIG. 12 is a schematic perspective view of the egg transfer system of FIG. 2, illustrating the transfer head ascending to a ready position;

FIG. 13 is a schematic perspective view of the egg transfer system of FIG. 2, illustrating removal of the hatching basket, with viable eggs, from the transfer system;

FIG. 14 is a schematic perspective view of the egg transfer system of FIG. 2, illustrating removal of the flat from the transfer system;

FIG. 15 is a schematic view of a transfer head assembly and its associated systems in communication with a classification device, according to one aspect of the present disclosure;

FIG. 16 is a schematic cross-section view of a lifting device of a transfer head assembly, according to one aspect of the present disclosure;

FIG. 17 is a schematic cross-section view of a lifting device having a valve actuator, according to one aspect of the present disclosure;

FIG. 18 is a schematic cross-section view of the lifting device of FIG. 17, illustrating actuation of the valve actuator to engage a stalk, according to one aspect of the present disclosure;

FIG. 19 is a schematic cross-section view of an alternative lifting device having a valve actuator, according to another aspect of the present disclosure;

FIG. 20 is a schematic cross-section view of the lifting device of FIG. 19, illustrating actuation of the valve actuator to engage a stalk, according to one aspect of the present disclosure;

FIG. 21 is a schematic cross-section view of an alternative lifting device having a valve actuator, according to yet another aspect of the present disclosure;

FIG. 22 is a schematic cross-section view of the lifting device of FIG. 21, illustrating actuation of the valve actuator to engage a stalk, according to one aspect of the present disclosure;

FIG. 23 is a side view of an egg processing system having an egg transfer system coupled with an injection apparatus for injecting eggs with a treatment substance, according to one aspect of the present disclosure;

FIG. 24 is a schematic perspective view of a transfer head assembly for an egg transfer system, according to one aspect of the present disclosure; and FIG. 25 is a magnified view of a cross-section of the transfer head assembly shown in FIG. 24.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

FIGS. 1 and 2 illustrate a transfer system 10 capable of transferring or otherwise sorting eggs in accordance with various aspects of the present disclosure. Aspects of the present disclosure are not limited to the illustrated transfer system 10. In some instances, the transfer system 10 may be particularly adapted for use in transferring eggs positioned within a setter incubator tray 20 (so-called "flat"), which include a plurality of receptacles for individually receiving and maintaining the eggs in a generally vertical orientation. Examples of suitable commercial flats include, but are not limited to, a "CHICKMASTER 54" flat, a "JAMESWAY 42" flat and a "JAMESWAY 84" flat (in each case, the number indicates the number of eggs carried by the flat). Using the transfer system 10, the eggs may be transferred from the flat 20 to a hatch incubator tray 30 (so-called "hatching basket"), which may be configured as an open-ended container. In general, the chicks are hatched in the hatching baskets, which require an open space configuration that allows the newborn chicks to hatch and move about, in contrast to the flats 20. Thus, systems (both manual and automated) are needed to transfer the eggs from the flats 20 to the hatching baskets 30 efficiently at high throughput speeds.

According to some aspects, the transfer system 10 may include a frame 15 and a conveyor assembly 40 provided to move the flats through the transfer system 10 to a transfer position in an automated manner. The conveyor assembly 40 may include a guide rail system 50 configured to receive and guide the flats 20 to the transfer position. The conveyor assembly 40 may further include appropriate stop elements, sensors, belts, endless loops, motors, etc. for proper indexing and positioning of the flats 20 within the transfer system 10. In some instances, the flats 20 may be manually advanced through the transfer system 10. In such instances, the guide rail system 50 may be provided to ensure guiding and locating of the flats 20 at the transfer position.

Eggs entering the transfer system 10 via the flat 20 may have varying classification characteristics. For example, the flats 20 may include eggs that are classifiable based on viability, pathogen content, genetic analysis, or combinations thereof. As such, aspects of the present disclosure relate to capabilities of the transfer system 10 to sort and transfer eggs according to such classifications. Classification of the eggs into subsets may be achieved using any suitable classification device(s) for indentifying eggs according to, for example, viability, pathogen content, genetic analysis, or combinations thereof. Such classification devices may be provided as part of the transfer system 10 or, in other instances, may be provided as part of an egg processing system 500 (FIG. 23) incorporating the transfer system 10, as described further herein. Exemplary classification devices may be capable of classifying the eggs by using, for example, candling techniques (opacity, infrared, NIR, etc.), assaying techniques, or other known and suitable classification methods, processes, or techniques. According to one aspect of the present disclosure, as shown in FIG. 2, the transfer system 10 may include a classification device 60 coupled to the frame 15 and capable of classifying the eggs. As the eggs are conveyed through the transfer system 10, the eggs interact with the classification device 60 for identification thereof.

After classification, the eggs may then be sorted and/or transferred accordingly using the transfer system 10. According to aspects of the present disclosure, the transfer system 10 may be configured to selectively sort and/or transfer eggs according to a selective release scheme. In this regard, the transfer system 10 may be capable of concurrently lifting or otherwise concurrently removing from the flat 20 eggs having various classification characteristics. In some instances, all eggs in the flat 20 may be removed therefrom, while in other instances less than all the eggs in the flat 20 may be removed. In this regard, at least some of the eggs may remain in the flat 20 for a variety of reasons, either intentionally or unintentionally. In any instance, the eggs removed from the flat 20 may have at least more than one classification characteristic among them such that the removed eggs are capable of being classified into subsets of eggs.

For example, the removed eggs may be a mix of eggs having either a viable or non-viable classification status, or a mix of eggs having a male or female classification status. As such, the transfer system 10 may be capable of selectively releasing the subsets of eggs separately from a lifting or removal means according to the classification status for each such that the eggs may be sorted according thereto. For example, the viable eggs may be released separate from the non-viable eggs such that the viable and non-viable eggs may be discretely processed. In this particular instance, the viable eggs may be transferred to the hatching basket 30 for placement in a hatcher incubator, while the non-viable eggs may be transferred to other processing means. As such, aspects of the present disclosure advantageously facilitate flexible processing of eggs by sorting and/or transferring thereof according to classification and using selective release means.

In some instances, there may only be two subsets of eggs as identified with the classification device 60. For example, the eggs may be divided into a first subset of viable eggs and a second subset of non-viable eggs, or a first subset of male eggs and a second subset of female eggs. However, aspects of the present disclosure provide the capability to manage more than two subsets as classified by one or more classification devices. For example, the classification device 60 or an additional classification device may be capable of further determining non-viable eggs as either clear (infertile) or dead (dead embryo). In such an instance, the viable eggs, the clear eggs, and the dead eggs may be selectively released separately such that each subset may be independently sorted and processed.

As shown in FIGS. 1 and 2, the transfer system 10 may include a transfer head assembly 70 coupled to the frame 15 and configured to move vertically for removing eggs from the flat 20 when the flat 20 is in the transfer position beneath the transfer head assembly 70. In some instances, the transfer head assembly 70 may be capable of lateral movement outside the conveyor assembly 40 and/or the transfer position. The transfer head assembly 70 may include a plurality of removal or lifting devices 80 in fluid communication with a manifold 90 such that the lifting devices 80 may commonly receive a vacuum or negative air pressure for lifting the eggs in contacting relationship with the lifting devices 80 for removal from the flat 20. The manifold 90 may be formed using opposing plates 95, 100 coupled to form a chamber 45 capable of being air-tight for holding a vacuum. The plates 95, 100 may be coupled together with any suitable attachment means, including, for example, latches, clamps, linkages, bolts, and fasteners. In some instances, the plate 95 may be removable from the plate 100 to allow for cleaning thereof.

A vacuum blower device 110 may be in fluid communication with the manifold 90 to supply negative air pressure thereto for facilitating removal of the eggs from the flat 20 using the lifting devices 80. In some instances, the vacuum blower device 110 may also be capable of providing positive air pressure to the manifold 90 for facilitating a common release of all eggs in contact with the lifting devices 80. That is, the vacuum blower device 110 may be capable of switching between supplying negative air pressure and positive air pressure to the manifold 90 (and all the lifting devices 80) so as to achieve a desired action (lift all eggs or release all eggs). While simply eliminating the vacuum would be sufficient to release the eggs from the lifting devices 80, at least some positive air pressure may be desirably applied to ensure the eggs are released from the lifting devices 80 in a consistent and controllable manner. The vacuum blower device 110 may be in fluid communication with the manifold 90 using tubing 115 or other suitable fluid connection means.

The transfer head assembly 70 may be pneumatically driven to move vertically for removing and lifting the eggs from the flat 20. As mentioned previously, the transfer head assembly 70 may also be configured to move laterally using, for example, pneumatics. In some instances, the transfer head assembly 70 may be lowered and raised pneumatically using a transfer cylinder 120 in fluid communication with a pneumatic system, as known by those of skill in the art, along with guide shafts 130 for guiding the transfer head assembly 70.

As shown in FIG. 2, a control unit 140 may have a controller 150 (FIG. 15) that is in communication with transfer head assembly 70. The controller 150 may be configured to receive, either directly or indirectly, a classification signal related to the classification status from the classification device 60 for each egg in the flat 20. The controller 150 may be configured to direct the transfer head assembly 70 to selectively release desired subsets therefrom. In this regard, the controller 150 may be capable of directing individual control of each lifting device 80 such that the eggs may be individually and selectively released from the transfer head assembly 70 separately. In some instances, the controller 150 may direct a positive air pressure system 220 (FIG. 15) or actuation of valves to individually control release of the eggs by each lifting device 80. According to some aspects, the controller 150 may be configured to direct lateral and/or vertical movement (i.e., raising and lowering) of the transfer head assembly 70.

FIGS. 2-14 illustrate a sequence of operations for an exemplary transfer system 10. In the exemplary transfer system 10, a plurality of eggs 25 are classified using a classification device 60 employing light measuring (candling device), in which light is transmitted through an egg and assessed by a light detector. The eggs 25 may be identified as either viable or non-viable. The light detectors may be operatively connected directly to the controller 150 (which may be a microprocessor or other programmable or non-programmable circuitry) or to another controller capable of transmitting the information to the controller 150 such that the controller 150 receives the classification status indirectly.

As shown in FIGS. 2 and 3, the conveyor assembly 40 moves the eggs 25 stored in the flat 20 past the classification device 60 so that each egg 25 passes therethrough and data (egg classification status) may be generated for each egg 25. The data collected by the classification device 60 may be provided to the controller 150 (or another controller) for processing and storing data associated with each egg 25. The controller 150 may then be capable of generating a selective release signal to send to the transfer head assembly 70 or associated systems so that individual eggs 25 (or subsets of eggs) are separately released based on the data collected by the classification device 60.

As shown in FIG. 4, the flat (or flats) 20 of eggs may be conveyed to the transfer position beneath the transfer head assembly 70. In some instances, the transfer head assembly 70 may be capable of processing multiple flats 20 at a time. With the flat (or flats) 20 properly positioned, the manifold 90 may be lowered to allow each lifting device 80 to locate and seal on a respective egg 25, as shown in FIG. 5. Vacuum may then be generated by the vacuum blower device 110 such that the eggs 25 are suctioned against the lift devices 80. As shown in FIG. 6, the transfer head assembly 70 may be raised by the transfer cylinder 120 such that the eggs 25 are removed and lifted from the flat 20. One or more weights 35 may be used to put weight on the flat 20 while the eggs 25 are lifted so as to keep the flat 20 on the conveyor assembly 40. Once removed from the flat 20, the eggs 25 may be lifted, lowered or released (selectively or non-selectively) by the transfer head assembly 70 in various manners, sequences, or steps according to a desired processing scheme implemented on the transfer system 10. For example, a processing scheme may be implemented to discard non-viable eggs and to transfer viable eggs to a hatching basket 30.

As shown in FIG. 7, the transfer system 10 may include an egg discard receptacle 160 attached to or otherwise operably engaged with the frame 15. The egg discard receptacle 160 may be configured to laterally translate beneath the transfer head assembly 70 along a rail assembly 170. In this regard, the egg discard receptacle 160 may be positioned to receive the non-viable eggs selectively released by the transfer head assembly 70. In some instances, the transfer head assembly 70 may be lowered closer to the egg discard receptacle 160 prior to selective release, while in other instances the transfer head assembly 10 may remain generally stationary until selective release once the egg discard receptacle 160 is positioned therebeneath. In some instances, as previously mentioned, the transfer head assembly 70 may be capable of moving laterally such that the egg discard receptacle 160 remains in a stationary position to receive the non-viable eggs, rather than moving beneath the transfer head assembly 70.

According to some aspects, the egg discard receptacle 160 has a plurality of walls 180 to prevent eggs from rolling off. The walls 180 may cooperate to define an opening 190 that allows the non-viable eggs to exit the egg discard receptacle 160. In some instances, the egg discard receptacle 160 may be configured to rotate or otherwise tilt when moving out from underneath the transfer head assembly 70 so as to assist in directing the eggs toward the opening 190. For example, a roller track or four-bar linkage may be implemented so as to cause the egg discard receptacle 160 to tilt as the egg discard receptacle 160 moves outward from under the transfer head assembly 70. The non-viable eggs exiting the egg discard receptacle 160 may be directed to a trash receptacle, a container, a conveyor for further processing, or any other processing means. While illustrating and describing the present disclosure with respect to removal of non-viable eggs from the transfer system 10, it will be appreciated that the egg discard receptacle 160 may be used to receive any classification of egg for directing the processing thereof.

FIGS. 9 and 10 illustrate loading of the hatching basket 30 onto a basket rail assembly 200 for advancement to a position beneath the transfer head assembly 70 and above the flat 20. In some instances, the basket rail assembly 200 may be disposed below the rail assembly 170 on the frame 15, but elevated above the flat 20 transfer position. In this regard, the hatching basket 30 may be loaded below the egg discard receptacle 160. Once positioned below the transfer head assembly 70, the hatching basket 30 is ready to receive viable eggs held by the lifting devices 80. As such, the transfer head assembly 70 may be lowered proximate to the hatching basket 30 such that breakage of the eggs is minimized or otherwise limited upon release thereof into the hatching basket 30, as shown in FIG. 11.

Release of the viable eggs into the hatching basket 30 may be achieved either selectively or non-selectively. For selective release, the controller 150 may indicate to the transfer head assembly 70 which eggs (viable) are selected for release, as similar to selective release of the non-viable eggs. Non-selective release may be accomplished in any number of ways. For example, the vacuum to the manifold 90 may be cut off such that the lifting devices 80 no longer provide suction to the eggs. In some instances, the vacuum blower device 110 may be switched to supply positive air pressure to the manifold 90 (and lifting devices 80) to control and ensure release of all remaining eggs. Other non-selective release means include supplying positive air pressure individually to each lifting device 80 concurrently, rather than commonly using the manifold 90.

As shown in FIG. 12, upon release of the eggs into the hatching basket 30, the transfer head assembly 70 may be raised to a ready position for processing of a subsequent flat(s) 20. As shown in FIG. 13, the hatching basket 30 may be removed from the transfer system 10 and placed in a hatching rack (not shown) for transportation to the hatching incubator. As shown in FIG. 14, the flat 20 may be removed from the transfer system 10 to allow for a subsequent flat 20 to advance to the transfer position. The flat 20, hatching basket 30, and egg discard receptacle 160 may be inserted and removed from any side of the transfer system 10, and the present disclosure is not limited to the illustrated aspects.

FIG. 15 illustrates the manifold 90 formed using opposing plates 95, 100 to form the chamber 45 therebetween. The plates 95, 100 may be coupled together with latches 210 that allow the plate 95 and, in some instances, the lifting devices 80 (when coupled thereto) to be removed for cleaning. The lifting devices 80 may be operably engaged with the manifold 90 such that the lifting devices 80 are in common fluid communication with the chamber 45 and the vacuum blower device 110. According to one aspect of the present disclosure, the lifting devices 80 may be individually in fluid communication with a positive air pressure system 220 such that positive air pressure may be individually applied to each lifting device 80. The positive air pressure system 220 may include pumps, valves, tubing, etc. for supplying positive air pressure to the lifting devices 80. In some instances, the lifting devices 80 may include valves for facilitating selective release therefrom. In some instances, the positive air pressure system 220 may be in communication with the controller 150 so as to receive control instructions regarding the supply of positive air pressure to selected lifting devices 80 for selective release of eggs. As described previously, the controller 150 may be in communication with the classification device 60, either directly or indirectly, so as to receive classification data therefrom.

According to one aspect, as shown in FIGS. 24 and 25, the lifting devices 80 may be operably engaged with the manifold 90 such that the lifting devices 80 are in common fluid communication with the chamber 45 and the vacuum blower device 110 (not shown) or otherwise a vacuum only system. According to one aspect of the present disclosure, the lifting devices 80 may be individually in fluid communication with a positive air pressure system 220 (not shown) such that positive air pressure may be individually applied to each lifting device 80. In one particular aspect, an opening of the lifting device 80 may be positioned within the chamber 45. The vacuum within the chamber 45 may be common to all the lifting devices 80 such that the lifting devices 80 only lift a respective egg when the lifting device 80 is moved proximate to the egg by the positive air pressure system 220. In some instances, the lifting devices 80 may have cylindrical rods 1000, which may be selectively actuated, for connecting to the positive air pressure system 220.

FIGS. 16-22 illustrate various lifting devices 80 configured to provide selective release capabilities to the transfer head assembly 70. In general, the lifting devices 80 may be commonly controlled to remove all eggs from the flat 20 by fluidly connecting the lifting devices with the vacuum blower device 110 via the manifold 90. Furthermore, the lifting devices 80 may be individually and independently controlled to facilitate selective release of the eggs and subsets thereof. In this regard, positive air pressure applied individually at a selected lifting device(s) 80 may be used to overcome the common vacuum applied via the manifold 90 to all the lifting devices 80. In the example of viable/non-viable eggs, non-viable eggs may be determined by an upstream classification device 60. Controls may be used to turn on a valve associated with each non-viable egg position at the transfer head assembly 70 so as to send positive pressure to that particular non-viable egg position. The positive pressure efficiently overcomes the vacuum in the lifting device such that the non-viable egg is selectively released, separate from the viable eggs. In some instances, the vacuum applied to the manifold 90 may range from about 3 psi to about 6 psi (or about 0.1 bar to about 0.5 bar; or 20 kPa to about 42 kPa, which are not exact conversions), while the positive air pressure applied to the lifting device 80 to overcome the vacuum and release the respective egg may be from a source of about 20 psi to about 100 psi (or about 135 kPa to about 700 kPa, which are not exact conversions), and typically between about 40 psi and about 60 psi (or about 275 kPa to about 415 kPa, which are not exact conversions), although the present disclosure is not limited to such stated ranges or values.

According to one aspect, as shown in FIG. 16, the plates 95, 100 may define a plurality of apertures 105 for receiving the lifting devices 80 such that the lifting devices 80 extend therebetween. The lifting device 80 may include a body 300 and a flange 305. The body 300 may be operably engaged with the plates 95, 100 of the manifold 90 such that at least a portion of the body 300 is disposed within the chamber 45. The flange 305 may be disposed exterior to the chamber to abut the plate 95. A sealing ring 310 (e.g., O-ring) may be disposed within the chamber 45 opposite the flange 305. A gasket 315 may be positioned to abut the plate 100 for sealing the body 300 about the apertures 105 of the plate 100. The body 300 may include a connector 325 integral or otherwise operably engaged therewith and/or with the flange 305. The lifting device 80 may include a flexible suction member (cup) 330 configured to contact, engage and lift the eggs using suction forces. According to one aspect, the flexible suction member 330 may be attached, connected, coupled or otherwise operably engaged with the connector 325. Apertures 105 in the plate 100 may allow individual connection of the lifting devices 80 to the positive air pressure system 220 using tubing 335, fluid connectors 340, fittings, valves, or other suitable pneumatic components. In some instances, valves may be placed on top of the manifold 90 to directly connect to the plate 100 without tubing.

With continuing reference to FIG. 16, the body 300 may define a fluid channel 320 extending therethrough between an inlet 345 and an outlet 350 such that the body 300 is in fluid communication with an interior 360 of the flexible suction member 330. In this manner, the flexible suction member 330 may receive the supply of positive air pressure that facilitates selective release of the eggs. The body 300 may further define a manifold channel 355 in fluid communication with the chamber 45 and the fluid channel 320 such that the interior 360 of the flexible suction member 330 is in fluid communication with the common supply of negative air pressure (applied by the vacuum blower device 110) used to lift the eggs from the flat 20. As previously described, selective release of the eggs may be achieved by individually supplying positive air pressure to selected lifting devices 80 so as to sufficiently overcome the negative air pressure commonly supplied to all lifting devices 80 via the vacuum blower device 110, as shown in FIG. 15. In other words, when positive air pressure is applied, pressure in the center of the body 300 (and the flexible suction member 330) may become slightly positive and the resulting small airflow will release the egg without causing loss of vacuum on other eggs.

FIGS. 17 and 18 illustrate another lifting device 80 capable of providing selective release capabilities to the transfer head assembly 70. According to this particular aspect, the positive air pressure efficiently overcomes the vacuum in the flexible suction member 330 by using a stalk 365 and valve actuator 370 configuration. FIGS. 19-22 illustrate similar configurations, but with differently configured stalks 365 and valve actuators 370. FIGS. 17, 19, and 21 illustrate the valve actuator 370 in a disengaged position, while FIGS. 18, 20, and 22 illustrate the valve actuator 370 in an engaged position such that positive air pressure is supplied to the flexible suction member 330. The configuration of FIGS. 17 and 18 illustrates the valve actuator 370 being disposed within a hollow portion of the stalk 365. The configuration of FIGS. 19 and 20 illustrates an end 375 of the stalk 365 disposed within the chamber 45 and being cone-shaped. The valve actuator 370 may be shaped to correspond to the end 375 for contact therewith. The configuration of FIGS. 21 and 22 illustrates the end 375 of the stalk 365 disposed within the chamber 45 and being cylindrically-shaped. The valve actuator 370 may be shaped to correspond to the end 375 for contact therewith.

In any instance, the stalk 365 may have a stalk channel 380 extending therethrough. The flexible suction member 330 may be attached to the lower end of the stalk 365, below the plate 95, to receive vacuum through the stalk 365 via the chamber 45. According to the aspects of FIGS. 17 and 18, at about the midpoint of the stalk 365, inside the chamber 45, may be a hole 385 defined by the stalk 365 and sized to provide sufficient vacuum from the chamber 45 to the stalk channel 380 and the flexible suction member 330 such that eggs are grabbed and held by the flexible suction member 330. The hole 385 may be sufficiently elevated above plate 95 to prevent egg residue collected on the plate 95 from plugging the hole 385 and/or the stalk channel 380. In other instances, such as illustrated in FIGS. 19-22, the end 375 of the stalk 365 may be sufficiently elevated above the plate 95 to achieve the same result such that the port to the stalk channel is elevated above the plate 95.

A valve assembly 390 may be provided about the aperture 105 of the plate 100 for providing positive air pressure to the lifting device 80. The valve assembly 390 may include a fitting 395 configure to receive tubing (not shown) for connecting the valve to the positive air pressure system 220. The valve assembly 390 may include the valve actuator 370. The valve actuator 370 may be configured to move in order to contact the stalk 365 when positive air pressure is applied to the lifting device 80 from the positive air pressure system 220. The valve actuator 370 may be normally biased using a biasing member 400 such that the stalk 365 and valve actuator 370 are non-engaging at the end 375, as shown in FIGS. 17, 19, and 21. When positive air pressure is applied to the lifting device 80, the valve actuator 370 moves to engage the stalk 365 so as to cover the stalk channel 380 within the chamber 45, thereby cutting off vacuum applied to the interior of the flexible suction member 330. As such, the egg held by the lifting device 80 may be selectively released due to the loss of suction (vacuum) force applied thereto.

As shown in FIG. 23, according to some aspects, the transfer system 10 may be provided as part of an egg processing system 500. In some instances, the egg processing system 500 may include an in ovo injection apparatus 600 configured to selectively or non-selectively inject eggs passing theretherough with a treatment substance such as, for example, vaccines, antibiotics or vitamins. In some instances, the injection apparatus 600 may actually be configured to remove material from avian eggs for various purposes, such as testing and vaccine harvesting. The injection apparatus 600 may comprise a plurality of injection devices that operate simultaneously or sequentially to inject a plurality of eggs. The injection apparatus 600 may comprise an injection head that comprises the injection devices, and wherein each injection device is in fluid communication with a source containing the treatment substance to be injected. The injection apparatus 600 may be designed to operate in conjunction with commercial flats. The flats may be transported through the injection apparatus 600 via an automated conveyor system for registering the flats beneath the injection head for injection of the eggs carried thereby In some instances, in ovo injection may be implemented selectively by the injection apparatus 600 such that the treatment substance is not dispensed into dead, infertile, or missing eggs. In this regard, a classification device may be used to classify the eggs in the flat conveyed through the injection apparatus 600 as viable or non-viable, or missing. As such, aspects of the present disclosure may include sending of the classification information determined by the classification device associated with the injection apparatus 600 to the controller 150, either directly or indirectly such that a separate classification device is not needed on the transfer system 10. In this regard, the classification device may be disposed upstream of the injection apparatus 600. Of course, in some instances, classification devices may be provided on both the injection apparatus 600 and the transfer system 10.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. For example, the selective release of eggs may be applied to a flat of eggs containing more than two subsets of eggs. Furthermore, aspects of the present disclosure may be combinable with selective removal means for selectively removing eggs from the flat. Such selective removal means may be implemented, for example, to remove viable eggs from the flat while maintaining non-viable eggs in the flat for disposal. In this regard, the lifting cups 80 may be individually controllable as previously described to provide positive air pressure to each flexible suction member 330 such that when the transfer head assembly 70 is raised from the flat 20 only a portion of the eggs is removed. That is, the lifting devices 80 may be applying positive air pressure such that the selected non-viable eggs do not receive suction force and thus are not lifted when the transfer head assembly 70 ascends. Although specific terms are employed herein, they are used in a generic and descriptive sense only and not for purposes of limitation.

That which is claimed:

1. An egg processing system, comprising:
    a frame;
    a controller configured to receive a classification signal indicative of an egg classification status for each of a plurality of eggs carried by an egg carrier;
    a transfer head assembly in communication with the controller and configured to remove a plurality of eggs from the egg carrier, the eggs being grouped into at least a first and second subset based on the egg classification status, the controller being configured to direct the transfer head assembly to selectively release the first and second subsets separately based on the respective egg classification status of the eggs;
    a conveyor assembly operably engaged with the frame, the conveyor assembly being configured to transport eggs beneath the transfer head assembly for removal from the egg carrier; and
    an egg discard receptacle operably engaged with the frame, the egg discard receptacle being configured to translate laterally between the transfer head assembly and the conveyor assembly to receive eggs of one of the first and second subset selectively released thereby.

2. An egg processing system according to claim 1, further comprising a classification device in communication with the controller and configured to classify the eggs according to the egg classification status.

3. An egg processing system according to claim 2, wherein the classification device is a candling device configured to classify the eggs according to egg opacity.

4. An egg processing system according to claim 2, further comprising an injection apparatus configured to inject a treatment substance into at least one of the first and second subsets based on the egg classification status prior to removal thereof by the transfer head assembly, wherein the classification device is disposed upstream of the injection apparatus.

5. An egg processing system according to claim 1, wherein the transfer head assembly comprises a plurality of lifting devices configured to individually and selectively release a respective egg held thereby.

6. An egg processing system according to claim 5, wherein each lifting device comprises:
    a flexible suction member adapted to engage an egg;
    a stalk operably engaged with the flexible member and adapted to connect the flexible suction member to a manifold of the transfer head assembly, the stalk having a stalk channel extending therethrough between a stalk inlet and a stalk outlet; and
    a valve actuator configured to pneumatically interact with the stalk to facilitate selective release of the egg engaged with the flexible suction member.

7. An egg processing system according to claim 1, wherein the transfer head assembly comprises:
    a plurality of lifting devices adapted to individually receive a supply of positive air pressure so as to facilitate selective release of a respective egg held thereby;
    a manifold operably engaged with the lifting devices and configured to commonly apply negative air pressure to the lifting devices so as to enable removal of the eggs from the egg carrier.

8. An egg processing system according to claim 7, wherein each lifting device comprises a body and a flexible suction member operably engaged therewith, the body defining a fluid channel extending therethrough between an inlet and an outlet such that the body is in fluid communication with the flexible member to receive the supply of positive air pressure, the body further defining a manifold channel in fluid communication with the manifold and the fluid channel such that the flexible suction member is capable of fluid communication with the supply of negative air pressure.

9. An egg processing system according to claim 1, further comprising a basket rail assembly operably engaged with the frame, the basket rail assembly being adapted to receive a hatching basket and configured to move the hatching basket in and out of position beneath the transfer head assembly, wherein the egg discard receptacle is disposed between the basket rail assembly and the transfer head assembly.

10. A method of processing eggs, the method comprising:
transporting a plurality of eggs in an egg carrier tray to a classification device;
classifying the eggs using the classification device so as to assign each egg an egg classification status, the eggs being classified as associated with one of a first subset and a second subset of the eggs according to the egg classification status;
transporting with a conveyor assembly the egg carrier tray to a position beneath a transfer head assembly for removal of the eggs from the egg carrier tray;
concurrently removing the first and second subsets of eggs from the egg carrier tray using the transfer head assembly;
replacing the egg carrier tray with a hatching basket positioning an egg discard receptacle between the conveyor assembly and the transfer head assembly;
selectively releasing one of the first and second subsets of eggs from the transfer head assembly onto the egg discard receptacle; and
releasing the other one of the first and second subsets of eggs from the transfer head assembly into the hatching basket.

11. A method according to claim 10, wherein classifying the eggs comprises classifying the eggs using a candling device as having one of a viable and non-viable status as the egg classification status such that one of the first and second subsets includes eggs with the viable status and the other of the first and second subsets includes eggs with the non-viable status.

12. A method according to claim 10, wherein classifying the eggs comprises classifying the eggs as having one of a male and female status as the egg classification status such that one of the first and second subsets includes eggs with the male status and the other of the first and second subsets includes eggs with the female status.

13. A method according to claim 10, further comprising the steps of generating a selective release signal based on the egg classification of each egg, and transmitting the selective release signal to a controller in communication with the transfer head assembly and configured to direct selective release of the first and second subsets of eggs.

14. A method according to claim 10, wherein replacing the egg carrier tray with a hatching basket comprises manually removing the egg carrier tray and moving the hatching basket into position beneath the transfer head assembly using a basket rail assembly.

15. A method according to claim 10, wherein concurrently removing the first and second subsets of eggs from the egg carrier tray using a transfer head assembly further comprises concurrently removing the first and second subsets of eggs from the egg carrier tray using negative air pressure commonly applied to a plurality of lifting devices of the transfer head assembly engaging the eggs.

16. A method according to claim 15, wherein selectively releasing one of the first and second subsets of eggs comprises individually cutting supply of the negative air pressure to respective lifting devices associated with the first and second subsets.

17. A method according to claim 15, wherein selectively releasing one of the first and second subsets of eggs comprises individually applying positive air pressure to respective lifting devices associated with the first and second subsets so as to overcome the negative air pressure being applied thereto, thereby causing the eggs to release from the respective lifting devices.

18. A method according to claim 15, wherein selectively releasing one of the first and second subsets of eggs comprises individually actuating a plurality of actuators associated with the lifting devices so as to apply positive air pressure to respective lifting devices associated with the first and second subsets so as to overcome the negative air pressure being applied thereto, thereby causing the eggs to release from the respective lifting devices.

* * * * *